(12) United States Patent
Branda et al.

(10) Patent No.: US 7,777,055 B2
(45) Date of Patent: Aug. 17, 2010

(54) PHOTOCHROMIC AND ELECTROCHROMIC COMPOUNDS AND METHODS OF SYNTHESIZING AND USING SAME

(75) Inventors: Neil R. Branda, North Vancouver (CA); Andrea Peters, Clifton Park, NY (US); Anthony J. Wigglesworth, Vancouver (CA)

(73) Assignee: Switch Materials Inc., Vancouver, B.C. (CA)

( * ) Notice: Subject to any disclaimer, the term of this patent is extended or adjusted under 35 U.S.C. 154(b) by 1135 days.

(21) Appl. No.: 10/523,965

(22) PCT Filed: Aug. 11, 2003

(86) PCT No.: PCT/CA03/01216

§ 371 (c)(1),
(2), (4) Date: Feb. 27, 2006

(87) PCT Pub. No.: WO2004/015024

PCT Pub. Date: Feb. 19, 2004

(65) Prior Publication Data

US 2006/0240197 A1    Oct. 26, 2006

Related U.S. Application Data

(60) Provisional application No. 60/402,081, filed on Aug. 9, 2002, provisional application No. 60/442,063, filed on Jan. 24, 2003.

(51) Int. Cl.
*C07D 333/50* (2006.01)
*C07D 409/14* (2006.01)

(52) U.S. Cl. .......................................... 549/49; 549/59

(58) Field of Classification Search ................. 348/902; 549/42, 59
See application file for complete search history.

(56) References Cited

U.S. PATENT DOCUMENTS

| | | | |
|---|---|---|---|
| 5,342,909 A | 8/1994 | Grubbs et al. | |
| 5,604,002 A | 2/1997 | Tsujioka et al. | |
| 5,736,065 A | 4/1998 | Nakaso et al. | |
| 5,849,851 A | 12/1998 | Grubbs et al. | |
| 6,123,952 A | 9/2000 | Lagrange | |
| 6,359,150 B1 | 3/2002 | Fukudome et al. | |
| 6,479,604 B1 | 11/2002 | Kim et al. | |
| 6,787,621 B2 | 9/2004 | Kim et al. | |
| 6,846,934 B2 | 1/2005 | Kim et al. | |
| 6,884,553 B2 | 4/2005 | Irie et al. | |
| 7,041,763 B2 | 5/2006 | Branda et al. | |
| 7,057,054 B2 | 6/2006 | Irie | |
| 7,101,497 B2 | 9/2006 | Tanaka et al. | |
| 7,135,132 B2 | 11/2006 | Kim et al. | |
| 2002/0142248 A1 | 10/2002 | Dubois | |
| 2003/0086978 A1 | 5/2003 | Kim | |
| 2003/0118924 A1 | 6/2003 | Kim | |

FOREIGN PATENT DOCUMENTS

| | | |
|---|---|---|
| CN | 1152110 | 6/2004 |
| EP | 446717 | 9/1991 |
| EP | 0 698 605 | 2/1998 |
| FR | 98 02123 | 8/1999 |
| JP | 64 22872 | 1/1989 |
| JP | 3264573 | 11/1991 |
| JP | 5112637 | 5/1993 |
| JP | 06 240242 | 8/1994 |
| JP | 8059651 | 3/1996 |
| JP | 08 119963 | 5/1996 |
| JP | 10 152679 | 6/1998 |
| JP | 11 256147 | 9/1999 |
| JP | 2002265465 | 9/2002 |
| WO | 9101312 | 2/1991 |
| WO | 9931107 | 6/1999 |
| WO | 0206361 | 1/2002 |
| WO | 2006125317 | 11/2006 |

OTHER PUBLICATIONS

Nees, D. Switching flow and phase behavior in surfactant systems via photochemical reactions. Progress in Colloid and Polymer Science. 101 (1996) 75-85.*

(Continued)

*Primary Examiner*—Kamal A Saeed
*Assistant Examiner*—Samantha L Shterengarts
(74) *Attorney, Agent, or Firm*—Chernoff, Vilhauer, McClung & Stenzel, LLP

(57) ABSTRACT

This invention relates to novel photochromic and electrochromic monomers and polymers based on 1,2-dithienylcyclopentene derivatives and method of using and synthesizing same. The compounds are reversibly interconvertible between different isomeric forms under suitable photochromic or electrochromic conditions. The electrochromic conversion may be catalytic. The application also relates to ultrahigh density homopolymers prepared using ring-opening methathesis polymerization (ROMP) where the central ring of the 1,2-bis(3-thienyl)-cyclopentene is incorporated directly into the polymer backbone. The monomer units may be readily functionalized to enable the synthesis of polymers with diverse structural and electronic properties. The compounds have many potential applications including high-density optical information storage systems, photoregulated molecular switches, reversible holographic systems, ophthalmic lenses, actinometry and molecular sensors, photochromic inks, paints and fibers and optoelectronic systems such as optical waveguides, Bragg reflectors and dielectric mirrors.

36 Claims, 9 Drawing Sheets

OTHER PUBLICATIONS

Asiri, A.M. et al., Kuwait Journal of Science and Engineering 1999, 26(2), 283-288.
Badland, M. et al., Chemical communications (Cambridge) 2000, (17), 1567-1568.
Bechinger, C.; Ferrere, S.; Zaban, A.; Sprague, J.; Gregg, B. A. Nature 1996, 383, 608.
Bolm, C.; Dinter, C. L.; Seger, A.; Hocker, H.; Brozio, J. J. Org. Chem. 1999,64,5730.
Buchholtz, F.; Zelichenok, A.; Krongauz, V. Macromolecules 1993,26,906.
Calcagno, P.; Karluki, B. M.; Kitchin, S.J.; Robinson, J. M. A.; Phillip, D.; Harris, K. D. M. Chem. Eur. J. 2000, 6, 2338.
Office Action dated Jan. 29, 2004, for U.S. Patent 7,041,763 (listed below).
Darcy, P. et al., Journal of the Chemical Society, Perkin Transactions 1: Organic and Bioorganic Chemistry (1972-1999) 1981, (1), 202-5.
Di Bella, S. Chem. Soc. Rev. 2001, 30, 355.
Fraysse et al., European Journal of Inorganic Chemistry 2000, 7, 1581-1590.
Gilat et al., J. Chem Soc., Chem. Comm. 1993, 1439-1442.
Gilat, S. L.; Kawai, S.H.; Lehn, J. M. Chem Eur. J. 1995, 1, 275.
Grubbs, R. H.; Tumas, W. Science 1989, 243, 907.
Heller, H. et al., Journal of the Chemical Society, Chemical Communication 1994, (23), 2713-14.
Heller, H. G. et al., Molecular Crystals and Liquid Crystals Science and Technology, Section A; Molecular Crystals and Liquid Crystals 1997, 297, 73-80.
Heller, H. G. et al., Molecular Crystals and Liquid Crystals Science and Technology, Section A; Molecular Crystals and Liquid Crystals 1994, 246, 79-86.
Ioyda, T.; Saika, T; Honda, K.; Schimidzu, , T. Tetrahedron Lett. 1989, 30, 5429.
Ireland, C. J.; Jones, K.; Pizey, J. S.; Johnson, S. Synth. Commun. 1976, 6, 185.
Irie, et al., Tetrahedron 1997, 53, 12263-12271.
Irie, M. Phosphorus, Sulfur and Silicon and the Related Elements 1997, 120 & 121, 95-106.
Irie, M.; Miyatake, O.; Uchida, K.; Eriguchi, T. J. Am. Chem. Soc. 1994, 116, 9894.
Irie, M.; Mohri, M. J. Org. Chem. 1988, 53, 803.
Ivanov, S. M.; Litchitskii, B. V.; Martynkin, A.Y.; Krayushkin, M. M. Chem. Heterocycl. Comp. 2001, 37, 85.
Kawai, S. H.; Gilat, S. L.; Ponsinet, R.; Lehn, J. M. Chem. Eur. J. 1995, 1, 285.
Kawai, T.; Kunitake, T.; Irie, M. Chem. Lett. 1999,905-906.
Kim et al., Macromolecules 1999, 32:4855-4860.
Koshido, T.; Kawai, T.; Yoshino, K. J. Phys. Chem. 1995, 99, 6110.
Kumar, G. S.; Neckers, D. C. Chem. Rev. 1989,89,1915.
Lucas, L. N.; Van Esch, J.; Kellogg, R. M.; Feringa,, B. L. Chem. Commun. 1998, 2313.
Lucas, L. N.; Van Esch, J.; Kellogg, R. M.; Feringa,, B. L. Tetrahedron Lett. 1999,1775-1778.
Lyubimov, A. V.; Zaichenko, N. C.; Marevtsev, V. S. J. Photochem. Photobiol. A : Chem. 1999, 120, 55.
Miki, S.; Noda, R.; Fukunishi, K. Chem Comm. 1997, 925.
Montalban, A. G.; Steinke, J. H. G.; Anderson, M. E.; Barret, A. G. M.; Hoffman, B. M. Tet. Lett. 1999,40,8151-8155.
Munakata, M.; Wu, L. P.; Kuroda-Sowa, T.; Maekawa, M.; Suenaga, Y.; Furuichi, K. J. Am. Chem. Soc. 1996,118,3305-3306.
Myles, A. J.; Branda, N. R. Macromolecules 2003, 36, 298.
Myles, A. J.; Branda, N. R. Org. Lett. 2000, 2, 2749.
Nakashima et al., Polymer Journal 1998, 30(12), 985-989.
Nakashima and Irie, Macromolecular Chemistry and Physics, (1999) vol. 200, Issue 4, pp. 683-692.
Nakayama, Y. et ali., Bulletin of the Chemical Society of Japan 1991, 64(1), 202-207.
Newell, A. K.; Utley, J. H. P. J Chem. Soc., Chem. Comm. 1992, 11: 800.
Norsten et al., Journal of the American Chemical Society 2001, 123(8), 1784-1785.
Peters et al., Chem. Comm. 2003, 954-955.
Robson, D.A.; Gibson, V. C.; Davies, R. G.; North, M. Macromolecules 1999, 32, 6371.
Saika, T.; Iyoda, T.; Honda, K.; Shimidzu, T. J. Chem. Soc. Perkin Trans. 2 1993, 1181.
Salakhov J. Org. Chem. USSR English Translation 1979, 2106-2112.
Sanford, M. S.; Love, J. A.; Grubbs, R. H. J. Am. Chem. Soc. 2001, 123, 6543.
Stellacci, F.; Bertarelli, C.; Toscan, F.; Gallazzi, M. C.; Zotti, G.; Zerbi, G. Advanced Materials, 1999, 64,292-295.
Takeshita, M.; Irie, M. J. Chem. Soc, Chem. Comm. 1996, 1807.
Takeshita, M.; Soong, C. F.; Irie, M. Tetrahedron Lett. 1998, 39, 7717.
Uchida et al., Chemistry Letters, The Chemical Society of Japan 2001, 4, 366-377.
Verbiest, T.; Houbrechts, S.; Kaurenen, M.; Clays, K.; Persoons, A. J.; Mater. Chem. 1997, 7, 2175.
Warshawsky, A.; Kahana, N.; Buchholtz, F.; Zelichonok, A.; Ratner, J.; Krongauz, V.; Ind. Eng. Chem. Res. 1995, 34,2825.
Wu, Z.; Benedicto, A. D.; Grubbs, R. H.; Macromolecules; 1993; 26; 4975.
Yu Lian-He, et al.; Youji Huaxue; 1993; 13(6); pp. 590-596.
Zhi, J. F.; Baba, R.; Hashimoto, K.; Fujishima, A.J.; Ber. Bunsenges. Phys. Chem.; 1995; pp. 99; 32.
Zhi, J. F.; Baba, R.; Hashimoto, K.; Fujishima, A.J.; Photochem. and Photobio. A 1995, 92, 91.
Ichimura, K.; In Organic Photochromic and Thermochromic Compounds; Crano, J. C., Gugliemetti, R.J., Eds.; Plenum Press: New York, 1999, vol. 2, pp. 9-63.
Irie, M.; in Molecular Switches, Feringa B. L., Ed.; Wiley-VHC: New York, 2001, p. 37.
Irie, M.; In Organic Photochromic and Thermochromic Compounds; Crano, J. C., Gugliemetti, R. J., Eds.; Plenum Press: New York, NY, 1999; vol. 1, Chapter 5, pp. 207-222.
Willner, I. et al., J. Am. Chem. Soc. 1992, 114, 3150-3151.
Irie, Masahiro, "Diarylethenes for Memories and Switches", Chem. Rev. 2000, 100, pp. 1685-1716.
Tsivgoulis, Gerasimos M., et al., "Photoswitched and Functionalized Oligothiophenes: Synthesis and Photochemical and Electrochemical Properties", Chemistry: A European Journal, vol. 2, No. 11, 1996, pp. 1399-1406.
Russian Chemical Bulletin, International Edition, vol. 50, No. 12, pp. 2420-2423, Dec. 2001.

* cited by examiner

PHOTOCHROMIC AND ELECTROCHROMIC COMPOUNDS AND METHODS OF SYNTHESIZING AND USING SAME

This application claims the benefit of U.S. provisional patent application Ser. No. 60/402,081 filed 9 Aug. 2002 and Ser. No. 60/442,063 dated 24 Jan. 2003.

FIELD OF THE INVENTION

This invention relates to novel photochromic and electrochromic monomers and polymers based on 1,2-dithienylcyclopentene derivatives and methods of using and synthesizing same.

BACKGROUND OF THE INVENTION

Molecules that toggle between two distinct forms when exposed to specific external stimuli, where each form exhibits unique physical properties, are promising candidates for fabricating controllable nano-devices.[1] Photochromic devices exhibit reversible variations in color when stimulated by light.[2] Few photochromic compounds possess the favourable properties displayed by the 1,2-dithienylcyclopentene skeleton, which interconverts between its colorless ring-open and colored ring-closed isomers with a high degree of fatigue resistance and bistability.[3] Photochromic compounds have many potential applications including high-density optical information storage systems, photoregulated molecular switches, reversible holographic systems, ophthalmic lenses, actinometry and molecular sensors, photochromic inks, paints and fibers and optoelectronic systems such as optical waveguides, Bragg reflectors and dielectric mirrors.[4]

[1] *Molecular Switches*, Feringa B. L., Ed.; Wiley-VHC: New York, 2001.
[2] *Oreganic Photochromic and Thermochromic Compounds*, Crano, J. C., Guglieметti, R. J., Eds.; Plenum Press: New York, 1999, Vols. 1 and 2.
[3] (a) Irie, M. In reference 1, p 37 (b) Irie, M. *Chem. Rev.* 2000, 100, 1685.

Electrochromic molecules which change color when electrochemically oxidized or reduced are also known in the prior art.[5] For example, electrochromic systems are used in optical display and optical shutter technology and are useful as variable-transmission filters. Electrochromic displays (ECDs) are potentially superior to cathode ray tube (CRT) and liquid crystal displays (LCDs) since they consume comparatively little power, exhibit display memory effects (i.e. persistence of an image after power is removed), and provide greater opportunities for varying image tone by applying a greater electrical charge. ECDs are also very flexible since the alignment of layers in a multi-layer device is not as critical. Composite electrochromic systems providing more flexibility in color may be readily designed. ECDs may also potentially be more useful than CRT and LCD technology for large-area displays and transmissive light modulators, such as windows and optical shutters.

[5] (a) Monk, P. M. S.; Mortimer, R. J.; Rosseinky, D. R. *Electrochromism: Fundamental and Applications*; VHC: New York, 1995. (b) Bechinger, C.; Ferrere,S.; Sprague, J.; Gregg. B. A. *Nature* 1996, 383, 608.

Heretofore "dual mode" compounds based on 1,2-dithienylcyclopentene skeleton that are both photochromic and electrochromic due to induced ring-closing/ring-opening reactions have not been described in the prior art.[6] Such dual mode compounds would offer the opportunity to fabricate more sophisticated and versatile control systems for regulating the optical properties of products. For example, composite systems comprising multiple layers can pose particular technical challenges. If all of the layers are solely photochromic, the light energy will be filtered once the first surface layer is colored and the likelihood of light penetrating all of the interior layers is low. Moreover, an interior layer cannot be independently addressed using light alone unless the system is capable of two-photon-mode photochromism. Electrochromism provides a means to access each layer individually since a multilayer device can be constructed of individual insulated electrode films. Many other applications may envisaged where it would be convenient to reversible change the color of a product by both photochromic and electrochromic means. It would be particularly advantageous if the electrochromic trigger could be implemented in a catalytic electrochemical process to minimize the required energy input.

[6] For examples of dual-mode photochromic/electrochromic hybrid systems, see (a) Miki, S.; Noda, R.; Fukunishi, K. *Chem Comm.* 1997, 925. (b) Zhi, J. F.; Baba, R.; Hashimoto, K.; Fujishima, A. *J photochem. and Photobia. A* 1995, 92, 91. (c) Zhi, J. F.; Baba, R.; Fujishima, A. *Ber. Bunsenges. Phys Chem.*1995, 99, 32. (d) Kawai, S. H.; Gilat, S.L.; Ponsinet, R.; Lehn, J. M. *Chem. Eur. J.* 1995,1, 285. (e) Saika, T.; Iyoda, T.; Honda, K.; Shimidzu, T. *J. chem. Soc. Perkin Trans.* 2 1993, 1181 (f) Newell, A.K.; Utley, J. H. P. *J Chem. Soc. Chem. Comm.* 1992, 800. (g) Ioyda, T; Honda, K.; Shimidzu, T. *Tetrahedron Lett.* 1989, 30,5429.

The need to incorporate photochromic and electrochromic molecules into workable materials such as films, sheets, fibers or beads demands them to be in polymeric rather than monomeric forms.[7] Ring-Opening Methathesis Polymerization (ROMP) is an ideal method for synthesizing functional polymers with narrow molecular weight distributions due to the mild reaction conditions needed and its compatibility with a wide range of functional groups.[8] In addition, the polymer chain length can be readily tailored by varying the catalyst/monomer ratio. The versatility of ROMP for generating photochromic polymers, including polymers having a variety of pendant functional groups, is described in the Applicant's PCT application No. PCT/CA01/01033 (WO 02/06361) which is hereby incorporated by reference. As described in the '033 application, homopolymers (i.e. polymers derived from one species of monomer) are more desirable than copolymers as they will have an increased density of the photochromic unit within the material.[9] This translates into a greater amount of information expressed or stored per unit volume or surface. While the photochromic homopolymers described in the '033 application are very useful, the density of the homopolymers is limited by the fact that the active photochromic component is located on a side chain of the polymer. In order to create ultra-high density homopolymers it would be desirable if the active component could be arranged directly on the main-chain or backbone of the polymer.

[7] Ichimura, K. In reference 2, Vol. 2, pp 9-63.
[8] Grubbs, R. H.; Tumas, W. *Science* 1989, 243, 907. (b) Sanford. M. S.; Love, J. A.; Grubbs, R. H. *J Am. Chem. Soc.* 2001. 123, 6543.
[9] (a) Myles, A. J.; Branda, N. R. *Macromolecules* 2003, 36, 298. (b) Myles, A. J.; Branda, N. R. *Org. Lett.* 2000, 2, 2749

A need has therefore arisen for dual mode compounds having physical properties which may be controlled be controlled both photochemically and electrochemically and improved homopolymers having a more dense arrangement of active chromic components, both in solution and in solid-state forms.

SUMMARY OF THE INVENTION

The invention relates to a compound selected from the group consisting of compounds reversibly convertible under photochromic and electrochromic conditions between a ring-open isomer (I) and a ring-closed isomer (II):

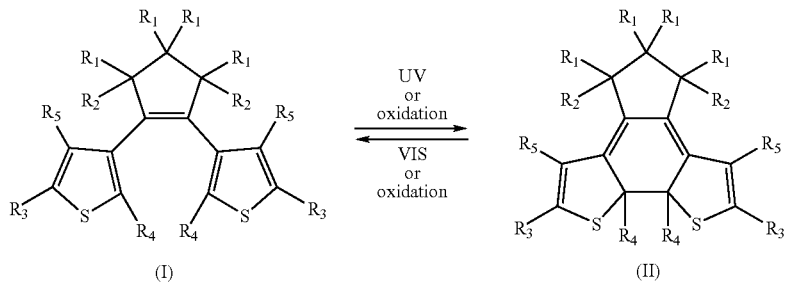

(I)            (II)

wherein $R_1$ is selected from the group consisting of H and a halogen; $R_2$ is selected from the group consisting of H, a halogen, CH=CH and a polymer backbone; $R_3$ is selected from the group consisting of H, a halogen, $CO_2Y$ (Y=H, Na, alkyl, aryl), and

(X=N,O,S); $R_4$ is selected from the group consisting of alkyl and aryl; and $R_5$ is selected from the group consisting of H, alkyl and aryl. In one embodiment of the invention $R_1$ and $R_2$ are preferably F. In another embodiment $R_1$ is H and $R_2$ forms part of a cyclic structure (i.e. $R_2$ is CH=CH).

goes a rapid ring-opening reaction to produce the radical cation of the ring-open isomer (I) which in turn readily accepts an electron from another molecule of the ring-closed molecule (II). Continuation of this oxidize/ring-open/reduce cycle will eventually result in the complete conversion of (II) to (I).

The compounds of the invention may be in either a monomeric or polymeric form. The polymeric form may be a homopolymer produced by ring-opening methathesis polymerization (ROMP). The homopolymer may include the active photochromic component as either a side-chain or the main-chain of the polymer. In the latter case the central ring of the photochromic 1,2-bis(3-thienyl)cyclopentene may be incorporated directly into the polymer main-chain to form an ultra-high density polymer interconvertible between isomeric forms (III) and (IV) as shown below:

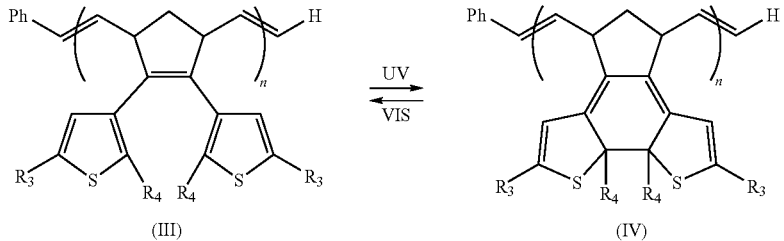

(III)            (IV)

The compounds of the group described above are "dual mode" since they are both photochromic and electrochromic under appropriate conditions. For example, a selected compound may be convertible from the ring-open isomer (I) to the ring-closed isomer (II) under photochromic conditions and from the ring-closed isomer (II) to the ring-open isomer (I) under electrochromic conditions. Conversely, the compound may be convertible from the ring-closed isomer (II) to the ring-open isomer (I) under photochromic conditions and from the ring-open isomer (I) to the ring-closed isomer (II) under electrochromic conditions. Moreover, the interconversion between the isomeric forms may be both photochromic and electrochromic depending upon what reaction conditions are selected. For example the compound may be convertible from the ring-closed (II) isomer to the ring-open isomer (I), or vice versa, under both photochromic and electrochromic conditions.

Preferably the electrochromic interconversion is catalytic. For example, oxidation of the ring-closed isomer (II) may result in the formation of a radical cation. The cation under-where $R_3$ is as described above and may, for example, consist of halogen, $CO_2CH_3$ or $CO_2H$.

BRIEF DESCRIPTION OF THE DRAWINGS

In drawings which illustrate embodiments of the invention but which should not be construed to limit the scope of the invention.

DETAILED DESCRIPTION OF THE INVENTION

Figure 1:
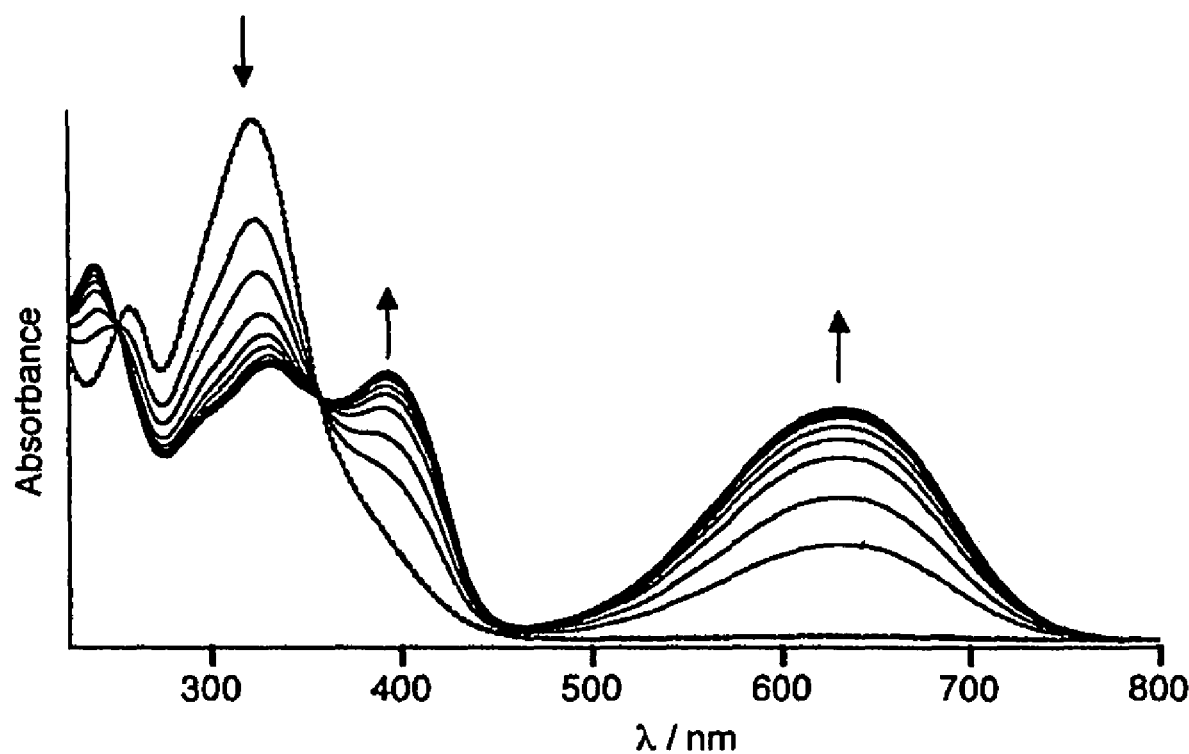
FIG. 1 is a graph of changes in the UV-Vis absorption spectrum of a $CH_2Cl_2$ solution of 1,2-bis(2,5-bis(2-thienyl)-3-thienyl)hexafluorocyclopent-1-ene (compound 1) ($2 \times 10^{-5}$ M) upon irradiation with 365 nm light. Irradiation periods are every 5 seconds until a 50 second period was reached. The dotted trace ( . . . ) is the spectrum after photobleaching the solution by irradiation with >490 nm light.

Throughout the following description specific details are set forth in order to provide a more thorough understanding of the invention. However, the invention may be practiced without these particulars. In other instances, well known elements have not been shown or described in detail to avoid unnecessarily obscuring the present invention. Accordingly, the specification and drawings are to be regarded in an illustrative, rather than a restrictive, sense.

This application relates to 1,2-dithienylcyclopentene derivatives having the general structure shown in Scheme 1 below:

Scheme 1

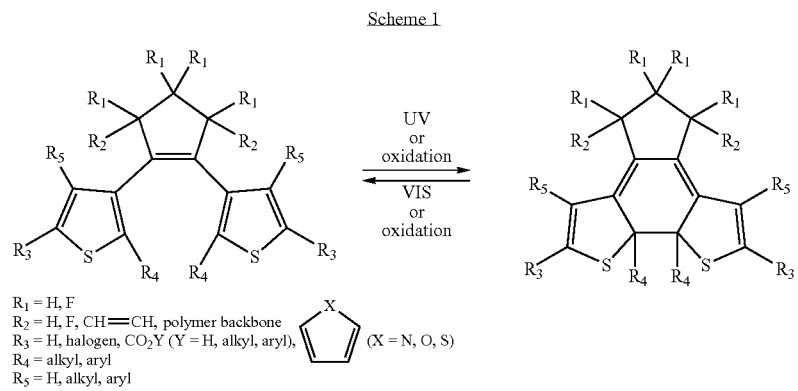

R$_1$ = H, F
R$_2$ = H, F, CH═CH, polymer backbone
R$_3$ = H, halogen, CO$_2$Y (Y = H, alkyl, aryl), (X = N, O, S)
R$_4$ = alkyl, aryl
R$_5$ = H, alkyl, aryl As described in detail below, this application also relates to methods of synthesizing and using the compounds, including both polymer and monomer precursors.

The compounds are reversibly convertible between the ring-open isomer (I) and the ring-closed isomer (II) under photochemical and/or electrochemical conditions. For example, reversible photocyclization between the ring-open and ring-closed forms (I, II) may occur when the compounds are irradiated with the appropriate wavelengths of light or electrochemically oxidized or reduced. For example, some compounds undergo photochemical ring-closing (with UV light) and both photochemical (with visible light) and electrochemical (oxidation) ring-opening. Conversely other compounds undergo photochemical ring-opening under photochemical conditions and ring-closing under both photochemical and electrochemical conditions. Accordingly, some of the compounds exhibit a dual-mode action combining both photochromism and electrochromism. As used in this patent application "photochromism" refers to the capacity of a compound to reversibly change color when subjected to radiant energy and "electrochromism" refers to the capacity to change color when subjected to a positive or negative charge. The general methodology for synthesizing the fluorinated derivatives of the invention is shown in Scheme 2. In this case octafluorocyclopentene is used as a reagent and $R_1$ and $R_2$ are F.

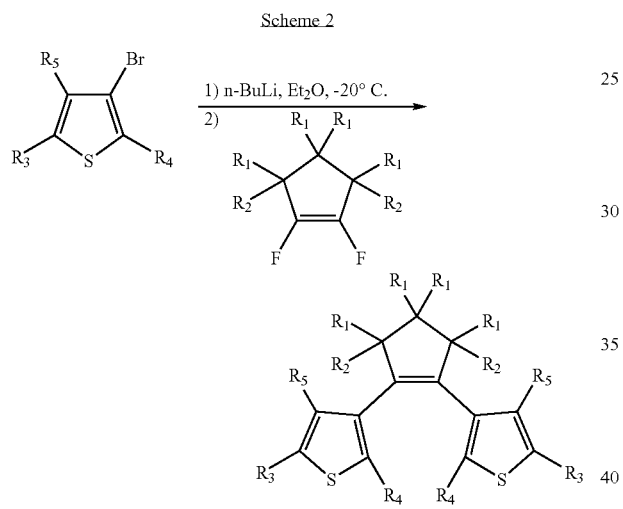

As shown Table 1, and as described in detail below, the following fluorinated monomeric compounds have been shown synthesized using the methodology of Scheme 2 and have been shown to exhibit both photochromic and electrochromic properties

TABLE 1

| Compound | $R_1, R_2$ | $R_3$ | $R_4$ | $R_5$ |
|---|---|---|---|---|
| 1 | F | ⟨furan⟩ X=S | ⟨furan⟩ X=S | H |
| 2 | F | H | ⟨furan⟩ X=S | H |
| 3 | F | ⟨phenyl⟩ | ⟨phenyl⟩ | H |
| 4 | F | H | ⟨phenyl⟩ | H |
| 5 | F | ⟨furan⟩ X=S | CH$_3$ | H |
| 6 | F | H$_3$C–⟨furan⟩ X=S | CH$_3$ | H |

As discussed above, the need to incorporate these compounds into workable materials such as films, sheets, fibers or beads demands that the compounds be in polymeric rather than monomeric forms. The fluorinated compounds may be polymerized using ring-opening methathesis polymerization (ROMP) as described in Patent Cooperation Treaty application No. PCT/CA01/01033 (WO 02/06361) and as shown generally in Scheme 3 below:

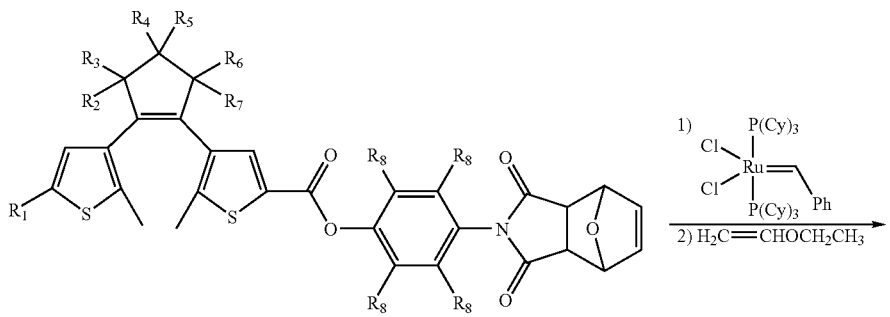

-continued

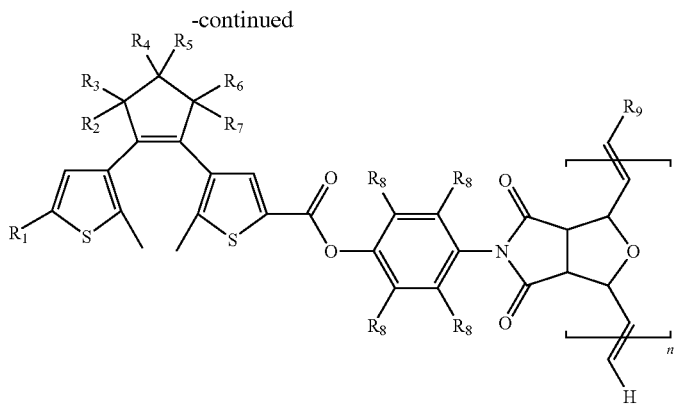

Another significant advantage of the invention is that the electrochromism of the photochromic compounds described herein is catalytic as shown in Scheme 4 below.

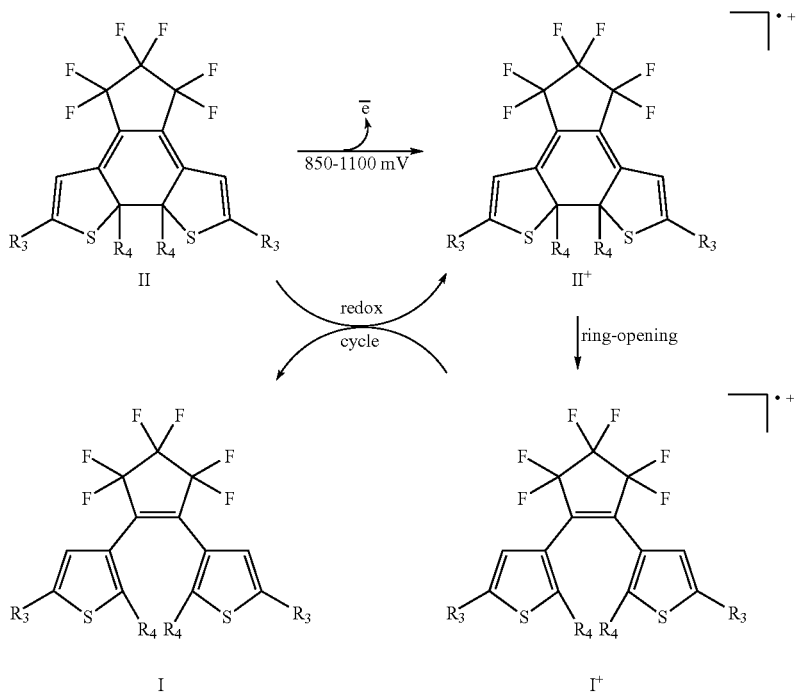

$R_3$ = H, alkyl, aryl
$R_4$ = aryl

In particular, in an electrochemical cell the ring-closed form (II) loses an electron to the anode (i.e. it is oxidized) and forms its radical cation. This radical cation undergoes a rapid ring-opening reaction to produce the radical cation of isomer (I). Because the neutral form of isomer (I) requires a substantially more positive potential to undergo oxidation (1.27 V), its radical cation immediately oxidizes a neighboring molecule of (II) and is effectively neutralized. Accordingly, only a small amount of the ring-closed form (II) needs to be oxidized because this will ring-open to (I), which will subsequently remove an electron from another molecule of (II) regenerating its radical cation. The continuation of this oxidize/ring-open/reduce cycle will eventually result in the complete conversion of (II) to (I).

The fact that the conversion between photochromic forms may be catalysed electrochemically may be advantageous in many applications of the invention, such as thin film displays. First, the need for diffusion of counterions is minimized which is often a kinetic bottleneck in conventional electrochromic systems. For example, in the case of an oxidation process, anions must be incorporated from the surrounding medium or cations must be ejected from the film to maintain charge balance. Typically this is accomplished by adding a secondary electrochrome and a charge-carrying layer to the system. This step is not required in the present case. The catalytic system needs minimal movement of ions because there is no net change in charge in the reactions or a buildup of charge. As described above, when the radical cation of the ring-open isomer forms, it removes an electron from a neighbouring molecule of the ring-closed isomer and hence the process will propagate throughout the entire system. Secondly, the catalytic process is very energy efficient since only a small amount of charge needs to be applied to initiate the catalytic cycle. Thirdly, the colouration value will be very large. The colouration value is proportional to the change in absorpitivity and inversely proportional to the charge injected per unit area. This is particularly important when constructing devices from indium tin oxide (ITO) electrodes which are semiconducting and have a very small number of charge carriers. In the case of films, very thin films such as monolayers do not contain a sufficient amount of active material to generate a satisfactory change in optical absorbance. Thicker films would require the diffusion of ions through all of the layers. The catalytic system of the present invention does not require diffusion since the transfer process can be relayed throughout the entire film. In other words the electrochemical trigger does not need to be highly efficient since it is only required to initiate the catalytic cycle.

The general methodology for synthesizing the non-fluorinated dithienylalkene derivatives using 2,3-dibromobicyclo [2.2.1]hepta-2,5-diene as a reagent is shown in Scheme 5 below.

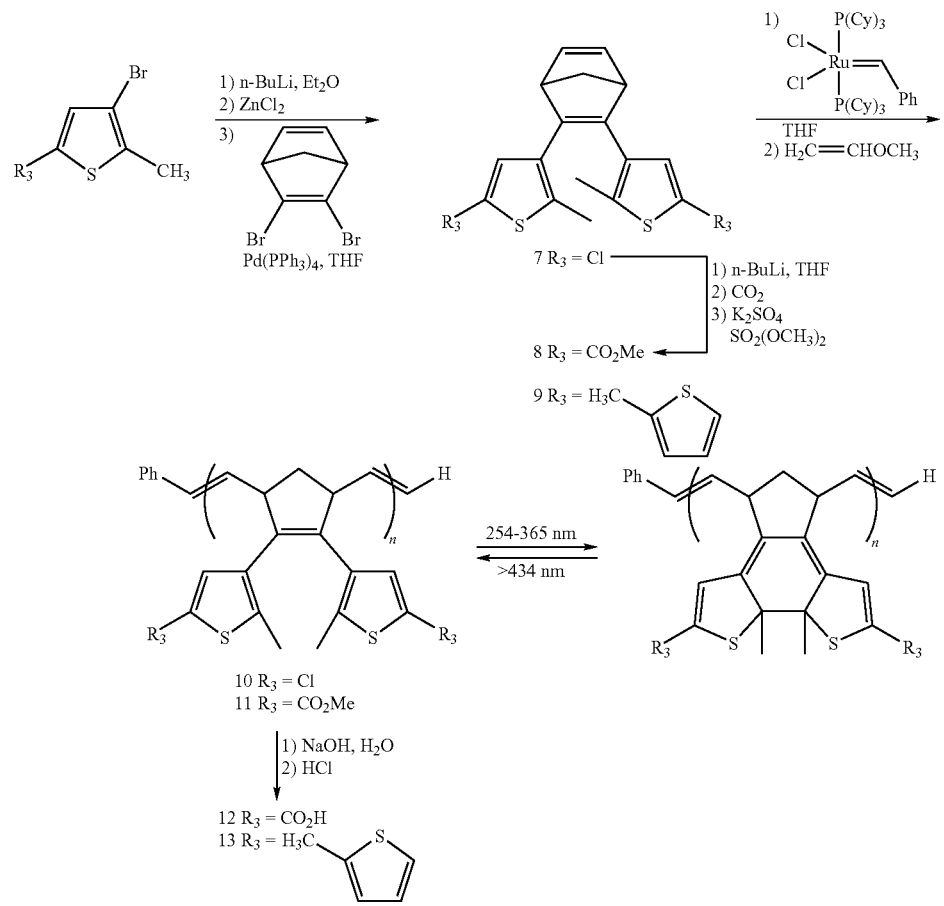

Scheme 5

As shown in Table 2, and as described in detail below, the following non-fluorinated monomeric and polymeric compounds have been shown synthesized using the methodology of Scheme 5.

TABLE 2

| Compound | $R_1$ | $R_2$ | $R_3$ | $R_4$ | $R_5$ |
|---|---|---|---|---|---|
| 7 | H | HC=CH | Cl | $CH_3$ | H |
| 8 | H | HC=CH | $CO_2CH_3$ | $CH_3$ | H |
| 9 | H | HC=CH | ![thiophene with H3C and X=S] | $CH_3$ | H |
| 10 | H | HC=CH polymer backbone | Cl | $CH_3$ | H |
| 11 | H | HC=CH polymer backbone | $CO_2CH_3$ | $CH_3$ | H |

TABLE 2-continued

| Compound | $R_1$ | $R_2$ | $R_3$ | $R_4$ | $R_5$ |
|---|---|---|---|---|---|
| 12 | H | HC=CH polymer backbone | $CO_2H$ | $CH_3$ | H |
| 13 | H | HC=CH polymer backbone | 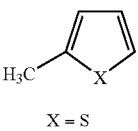 X = S | $CH_3$ | H |

An important advantage of the polymerization approach shown in Scheme 5 (for example, yielding polymerized compounds 10, 11 12 and 13) is that the cyclopentene ring of the 1,2-bis(3-thienyl)cyclopentene unit is incorporated directly into the polymer backbone. This results in a polymer having an ultra-high density of active photochromic/electrochromic components (i.e. higher densities are achieved by decreasing the size of the linker that connects the dithienylethene to the polymer backbone). Higher density polymers offer the opportunity to express or store a greater amount of information per unit volume or surface area. For example, the percent mass of the active photochromic component in the side-chain polymers shown in Scheme 3 ranges from 60-68%. By way of comparison, the new generation main-chain polymers of Scheme 5 have a percent mass of the active photochromic component ranging up to 93%. This is primarily due to the ROMP reaction of the strained olefin producing the requisite cyclopentene backbone that has been shown to be very versatile. As described below, both lipophilic and hydrophilic versions of the polymers have been prepared.

As described below, the photochromic polymers of Table 2 have been shown to undergo induced isomerization both in solution and in solid state form. These functional polymers are therefore well suited for incorporation into workable materials such as films, sheets, fibers or beads.

EXAMPLES

The following examples will further illustrate the invention in greater detail although it will be appreciated that the invention is not limited to the specific examples.

Experimental Methods

All solvents were dried and degassed by passing them through steel columns containing activated alumina under nitrogen using an MBraun solvent purification system. Solvents for NMR analysis (Cambridge Isotope Laboratories) were used as received. All synthetic precursors were purchased from Aldrich with the exception of $Pd(PPh_3)_4$ and bis(tricyclohexylphosphine)benzylidene ruthenium(IV) dichloride (Grubb's catalyst) which were purchased from Strem. Octafluorocyclopentene was obtained from Nippon Zeon Corporation. Column chromatography was performed using silica gel 60 (230-400 mesh) from Silicycle Inc.

$^1H$ NMR characterizations were performed on a Bruker AMX 400 instrument working at 400.103 MHz. $^{13}C$ NMR characterizations were performed on a Bruker AMX 400 instrument working at 100.610 MHz. Chemical shifts (δ) are reported in parts per million relative to tetramethylsilane using the residual solvent peak as a reference standard. Coupling constants (J) are reported in Hertz. FT-IR measurements were performed using a Nexus 670 or a Nicolet Magna-IR 750 instrument. UV-VIS measurements were performed using a Varian Cary 300 Bio spectrophotometer. Low resolution mass spectrometry measurements were performed using a HP5985 with isobutane as the chemical ionization source.

Standard lamps used for visualizing TLC plates (Spectroline E-series, 470 μW/cm²) were used to carry out the ring-closing reaction of all photochromic compounds using a 365-nm, a 313-nm or a 254-nm light source when appropriate. The compositions of all photostationarty states were detected using $^1H$ NMR spectroscopy. The ring-opening reactions were carried out using the light of a 150-W tungsten source that was passed through a 490-nm or a 434-nm cutoff filter to eliminate higher energy light.

As used herein, a bold numeral (e.g. 1) denotes the ring-open isomeric form of a compound and a bold, primed numeral (e.g. 1') denotes the ring-closed isomeric form of the same compound.

Example 1

1.1 Synthesis of 1,2-bis(2,5-bis(2-thienyl)-3-thienyl) hexafluorocyclopent-1-ene (Compound 1)

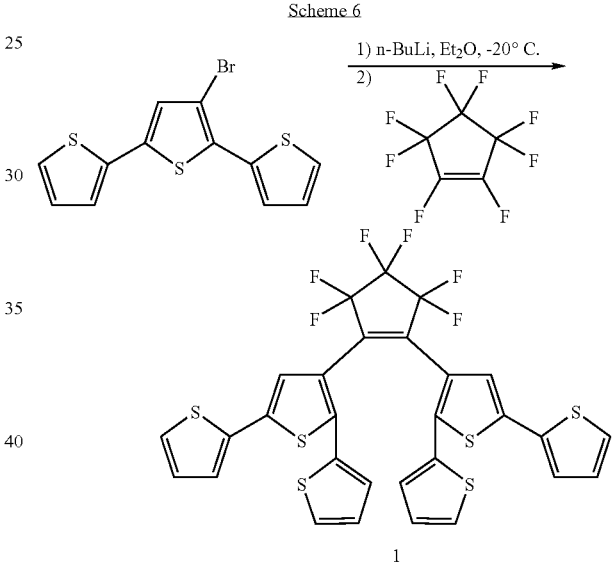

Scheme 6

A solution of 3'-bromo-2,2';5'2'terthiophene (0.749 g, 2.3 mmol) in anhydrous $Et_2O$ (25 mL) cooled to −20° C. was treated with n-BuLi (0.91 mL of a 2.5 M solution in hexane) dropwise under an argon atmosphere. After stirring the solution for 30 min, octafluorocyclopentene (0.13 mL, 1.15 mmol) was added dropwise using a cooled gas tight syringe and the solution immediately turned dark red in colour. After stirring for 1 h, the cooling bath was removed and the solution was allowed to warm to room temperature and stirred for 16 h when it was quenched with 5% HCl (10 mL). The aqueous layer was separated and extracted with $Et_2O$ (2×10 mL). All organic extracts were combined, washed with $H_2O$ (2×10 mL), followed by brine (10 mL), dried ($Na_2SO_4$) and filtered. The solvent was evaporated under reduced pressure and the crude product was purified using column chromatography through silica gel (hexanes) yielding 175 mg of pure product as a yellow crystalline solid. Yield: 23%.

M.p. 116-117° C.; $^1H$ NMR (300 MHz, $CD_2Cl_2$) δ 7.30 (dd, J=5, 1 Hz, 2H), 7.19 (dd, J=5, 1 Hz, 2H) 7.11 (dd, J=4, 1 Hz, 2H), 7.04 (dd, J=5, 4 Hz, 2H), 6.83 (dd, J=5, 3 Hz, 2H), 6.74 (dd, J=3, 1 Hz, 2H), 6.41 (s, 2H); $^{13}C$ NMR (125 MHz, $CD_2Cl_2$) δ 137.9, 136.3, 136.2, 133.0, 128.3, 128.2, 127.9, 127.0, 125.7, 125.0, 124.9, 123.8 (12 of 15 carbons found); FT-IR ($CHCl_3$ cast) 3105, 1695, 1685, 1651, 1644, 1616, 1576, 1561, 1538, 1505, 1467, 1415, 1384, 1328, 1274, 1244, 1225, 1191, 1130, 1096, 1046, 1028, 976, 952, 877, 833, 757, 696, 581, 553, 472, 458 $cm^{-1}$; HRMS (EI) Calcd for $M^+$ ($C_{29}H_{14}F_6S_6$): 667.9324. Found: 667.9337.

1.2 Synthesis of the Ring-Closed Form 1'.

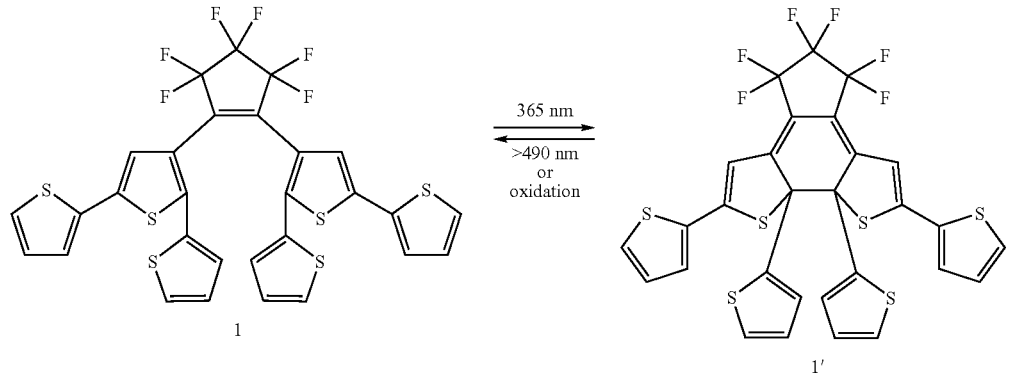

Scheme 7

Compound 1 (5 mg) was dissolved in $CH_2Cl_2$ (20 mL) and placed in a quartz glass cell. The solution was irradiated at 365 nm for 10 min. The solvent was evaporated off under reduced pressure and the crude product was recrystallized (hexanes) to afford the pure product as a blue powder.

$^1$H NMR (500 MHz, $CD_2Cl_2$) δ 7.49 (d, J=5 Hz, 2H), 7.38 (dd, J=4, 1 Hz, 2H), 7.30 (dd, J=5, 1 Hz, 2H), 7.28 (d, J=4 Hz, 2H), 7.07 (dd, J=5, 4 Hz, 2H), 6.92 (dd, J=5, 4 Hz, 2H), 6.58 (s, 2H).

1.3 UV-VIS Spectroscopy of Compound 1

Irradiation of a $CH_2Cl_2$ solution ($2\times10^{-5}$ M) of compound 1 with 365 nm light resulted in an immediate increase in the absorption band in the visible spectral region ($\lambda_{max}$=632 nm) due to the production of the ring-closed isomer 1' of compound 1 (FIG. 1). A visual change in colour from light yellow to blue accompanied this transformation. Subsequent irradiation of the solution with visible light (greater than 490 nm) resulted in the complete disappearance of the absorption band at 632 nm and regeneration of the original UV-VIS absorption trace representing the ring-open isomer 1.

1.4 Thermal Stability of the Ring-Closed Isomer 1'

The thermal stability of the ring-closed isomer 1' was studied by storing a sample containing 80% of the ring-closed isomer 1' (i.e. the photostationary state) in $CD_2Cl_2$ at room temperature in the dark. $^1$H NMR analysis was performed on this solution periodically and the ring-closed isomer 1' was thermally stable at 25° C. for over one month.

1.5 Cyclic Voltammetry of 1 and 1'

Figure 2:
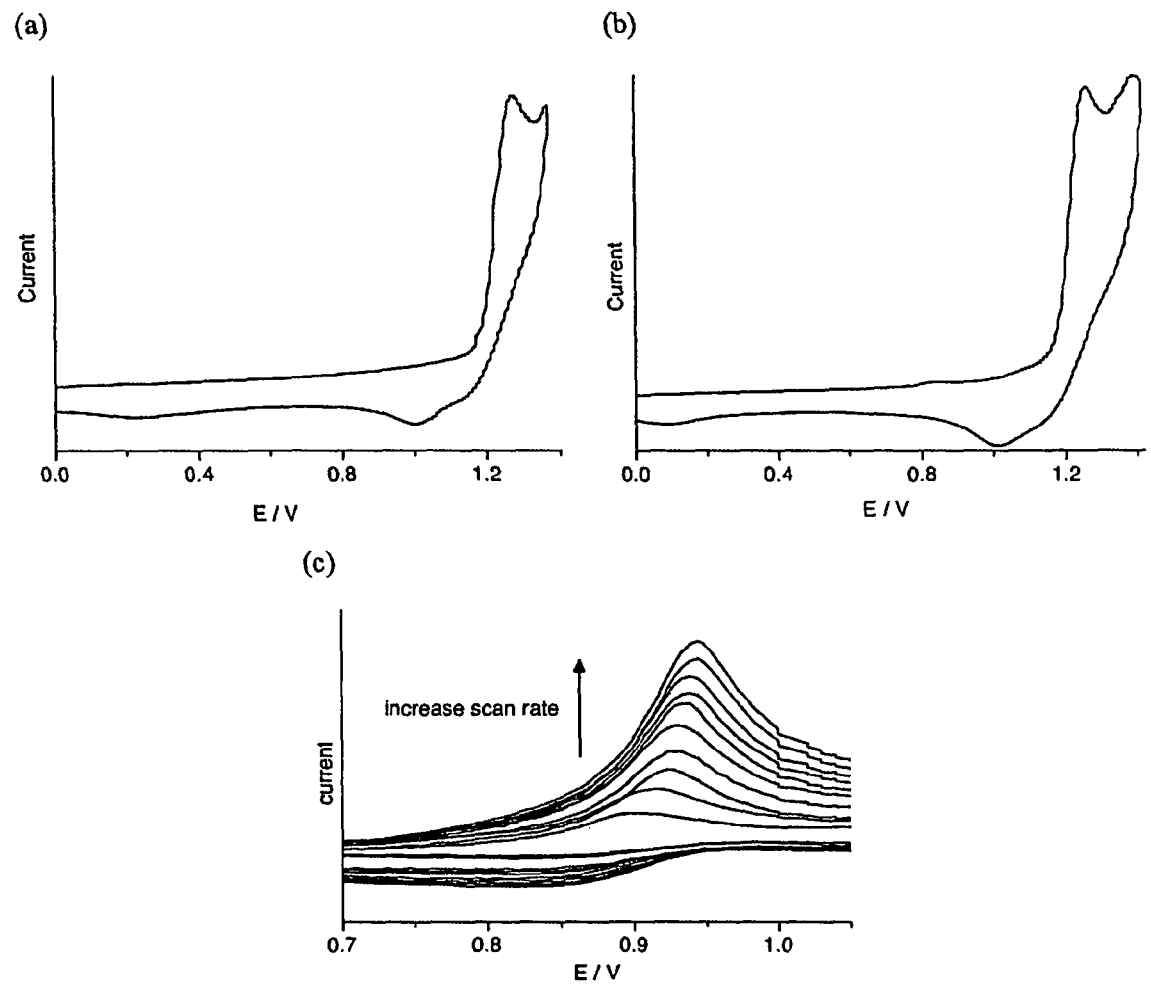
FIGS. 2(a)-2(c) are cyclic voltammograms of a $CH_3CN$ solution ($1 \times 10^{-3}$ M) of (a) compound 1 and (b) compound 1' at a scan rate of 200 mV/s with 0.1 M $NBu_4$ $PF_6$ as the supporting electrolyte. Graph (c) shows the partial cyclic voltammogram of a $CH_3CN$ solution ($1 \times 10^{-3}$ M) of 1' at scan rates of 50, 100, 150, 200, 250, 300, 350, 400, 450, and 500 mV/s. A platinum disk working electrode, a Ag/AgCl (in saturated NaCl) reference electrode and a platinum wire counter electrode were used. Ferrocene was added as an internal reference (0.405 V vs SCE).

The cyclic voltammogram of ring-open isomer 1 shows an irreversible oxidation peak at 1.27 V for all scan rates tested (50-3000 mV/s) (FIG. 2a). The voltammogram of the ring-closed isomer of compound 1', obtained after irradiation of a $CH_3CN$ ($1\times10^{-3}$ M) solution of compound 1 with 365 nm light for 5 minutes, showed a very small irreversible oxidation peak at 0.85 V that is almost too small to measure (FIG. 2b). Increasing the sweep rate in the cyclic voltammetry experiments resulted in a subsequent increase in the intensity of the oxidation peak at 0.85 V. However, there is insignificant growth in the reduction peak on the return sweep (FIG. 2c).

This implies that the rate of the ring-opening reaction of the radical cation compound $1'^{(+\bullet)}$ is faster than the limitations of our instrument. The sweep rate was increased up to a maximum speed of 5000 mV/s without a significant change in the intensity of the reduction peak on the return sweep.

Figure 3:
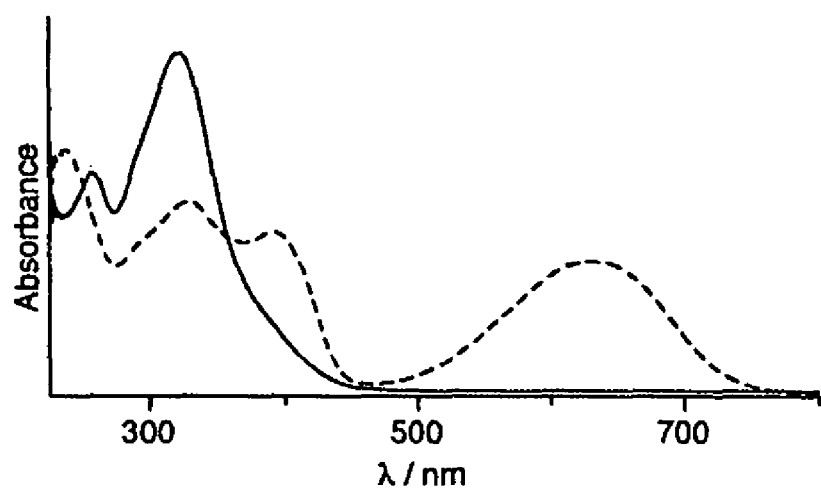
FIG. 3 is a graph of the UV-Vis absorption spectra of a $CH_2Cl_2$ solution ($2\times10^{-5}$ M) containing 75% of 1' before addition of the radical cation [(4-BrC$_6$H$_4$)$_3$N][SbCl$_6$]( - - - ) and after addition of one mole % [(4-BrC$_6$H4)$_3$N][SbCl$_6$] (—).
Figure 4:
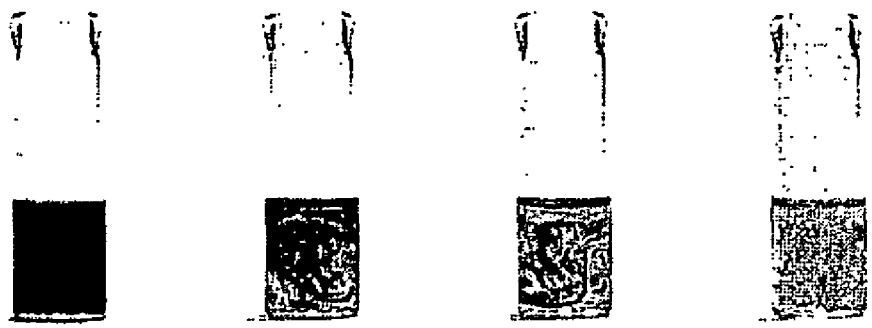
FIG. 4 is a series of photographs showing a gradual color change of a $CH_2Cl_2$ solution of compound 1 containing 75% of the ring-closed isomer 1' when treated with a catalytic amount of [(4-BrC$_6$H4)$_3$N][SbCl$_6$].

1.6 Catalytic Ring-Opening of Compound 1' Monitored Using UV-VIS Absorption Spectroscopy A $CH_2Cl_2$ solution of ring-open isomer 1 was irradiated with 365 nm light until 75% of the ring-closed form 1' was produced as determined by $^1$H NMR spectroscopy. The UV-VIS absorption spectrum of a $CH_2Cl_2$ solution containing 75% of the ring-closed isomer 1' is shown in FIG. 3. An aliquot of a $CH_2Cl_2$ solution ($2\times10^{-5}$ M) of the one-electron-accepting radical cation [(4-$BrC_6H_4$)$_3$N][$SbCl_6$] ($E_{ox}$=1.15 V), corresponding to one mol % was added to the blue $CH_2Cl_2$ solution containing 75% of the ring-closed isomer 1'. The V-VIS absorption spectrum taken immediately after the addition of one mol % of [(4-$BrC_6H_4$)$_3$N][$SbCl_6$] showed the complete disappearance of the absorption band in the visible region ($\lambda_{max}$=632 nm) corresponding to the ring-closed isomer 1' and regeneration of the spectrum that is consistent with the ring-open isomer 1 (FIG. 3 and FIG. 4). Irradiation of the solution with 365 nm light resulted in no change of the UV-Vis spectrum, which would accompany the formation of the ring-closed product, since the radical cation [(4-$BrC_6H_4$)$_3$N][$SbCl_6$] still remained in solution. Inducing the ring-opening reaction using a catalytic amount of the chemical oxidant was very efficient since only a small percent was needed to initiate the ring-opening process.

1.7 π-Conjugation

The π-electrons are delocalized throughout the photochromic backbone only in the ring-closed state 1' due to the linearly π-conjugated pathway that is created upon photocyclization. On the other hand, these electrons are forced to reside on the two thiophene rings in the ring-open form 1 due to the lack of linear π-conjugation between the two heterocycles. Therefore, any π-electrons of the two $R_3$ groups can only interact with each other through the conjugated pathway in the ring-closed state 1'. Accordingly, incorporating the photochromic dithienylethene backbone into polyene molecular wires should permit the reversible switching of conductive properties by photoirradiation. Although there are several reports that describe how this structural modification can regulate electronic communication between various $R_3$ substituent groups, the inventors are unaware of any that take advantage of the skeletal alteration between the groups $R_3$ and $R_4$ within the two isomers: upon photochemical ring closure, the two carbon atoms involved in forming the new single bond (the 2'-positions of the heterocycles) change their hybridization from $sp^2$ to $sp^3$.

In accordance with the invention two terthiophene units have been modified so that the central thiophene rings of each make up the photochromic dithienylethene backbone. Because oligo and polythiophenes display promising semiconducting properties and are being considered as prototype molecular-scale wires, the inventors chose to use terthiophene as a model oligothiophene to incorporate into the photochromic 1,2-dithienylcylcopentene. Complete delocalization of the π-electrons in this manner results in the ring-closed structure 1'. Using this approach, π-conjugation is not just regulated on command, but also re-routed.

Single crystals of compound 1 suitable for X-ray crystallographic analysis were grown by slowly cooling a hot hexane solution of the compound. The structure of 1 in the crystal reveals that the two peripheral heterocycles of each terthiophene are rotated an average of 20° and 48° for the outer and inner rings respectively. Despite this deviation from coplanarity with the central heterocycle in the solid-state, the recorded UV-Vis absorption spectra, described above, show that, in solution, π-conjugation is still extended throughout each terthiophene arm of the photochromic system.

This work clearly demonstrates that while the ring-open isomer 1 has two π-conjugated terthiophene arms, the ring-closed isomer 1' has the linearly π-conjugated pathway extending throughout the backbone of the photochrome. The original conjugated pathways have been destroyed. This is clearly evidenced by the similarity of the absorption spectrum in the visible region between the ring-closed forms of 1' and 5' (described further below), the latter possessing an identical linear π-conjugation backbone but is lacking the additional thiophene heterocycles. The absorption spectra of ring-open 1 and 5 are different due to the extended conjugation in 1 as compared to 5.

Similar principles apply in respect of the other compounds described below where $R_3$ and $R_4$ are aryl.

Example 2

2.1 Synthesis of 1,2-bis(2,2'-bithien-3-yl)hexafluorocyclopent-1-ene (compound 2).

Scheme 8

A solution of 3-bromo-[2,2']bithiophenyl (0.500 g, 2.3 mmol) in anhydrous $Et_2O$ (25 mL) cooled to −20° C. was treated with n-BuLi (0.82 mL of a 2.5 M solution in hexane) dropwise under an argon atmosphere. After stirring the solution for 30 min, octafluorocyclopentene (0.13 mL, 1.0 mmol) was added dropwise using a cooled gas tight syringe and the solution immediately turned dark red. After stirring at this temperature for 1 h, the cooling bath was removed and the reaction mixture was allowed to warm to room temperature and stirred for 16 h when it was quenched with 5% HCl (5 mL). The aqueous layer was separated and extracted with $Et_2O$ (2×10 mL). All organic extracts were combined, washed with $H_2O$ (2×10 mL), followed by brine (10 mL), dried ($Na_2SO_4$) and filtered. The solvent was evaporated under reduced pressure and the crude product was purified using column chromatography through silica gel (hexanes) yielding 75 mg of pure product as a white solid. Yield: 8%.

M.p. 160-162° C.; $^1$H NMR (400 MHz, $CD_2Cl_2$) δ 7.23 (dd, J=5, 1 Hz, 2H), 7.03 (d, J=5 Hz, 2H), 6.89 (dd, J=5, 4 Hz, 2H), 6.64 (dd, J=4, 1 Hz, 2H), 6.41 (d, J=5 Hz, 2H); $^{13}$C NMR (125 MHz, $CDCl_3$) δ 137.1, 133.2, 127.7, 127.5, 126.9, 126.3, 125.4, 124.3 (8 of 11 carbons found); FT-IR ($CH_2Cl_2$ cast) 3110, 2924, 2841, 1337, 1275, 1241, 1189, 1130, 1088, 963, 942, 852, 737, 699, 651 cm$^{-1}$; LRMS (CI) Calcd for M$^+$ ($C_{21}H_{10}F_6S_4$) 504. Found: 505 [M+H]$^+$. Anal. Calcd for $C_{21}H_{10}F_6S_4$: C, 49.99; H, 2.00. Found: C, 50.40; H, 2.11.

2.2 Synthesis of the Ring-Closed Form 2'

Scheme 9

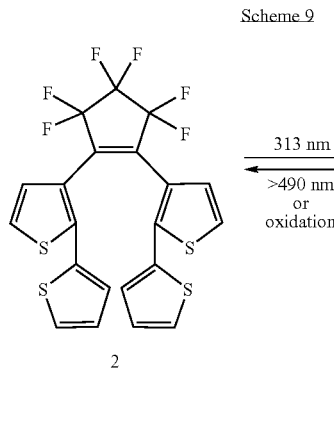

Compound 2 (10 mg) was dissolved in CH$_2$Cl$_2$ (20 mL) and placed in a quartz glass cell. The solution was irradiated with 313 nm light for 4 min. The solvent was evaporated under reduced pressure and the crude product was purified using column chromatography through silica gel (hexanes: CH$_2$Cl$_2$, 9:1) to afford pure 2' as a purple solid.

$^1$H NMR (600 MHz; CD$_2$Cl$_2$) δ7.42 (dd, J=3.6, 1.2 Hz, 2H), 7.34 (dd, J=4.8, 1.2 Hz, 2H), 7.14 (d, J=6.0 Hz, 2H), 6.96 (dd, J=5.4, 1.2 Hz, 2H), (d, J=5.4 Hz, 2H), 6.28 (d, J=6.0 Hz, 2H).

2.3 UV-VIS Spectroscopy of Compound 2

Figure 5:
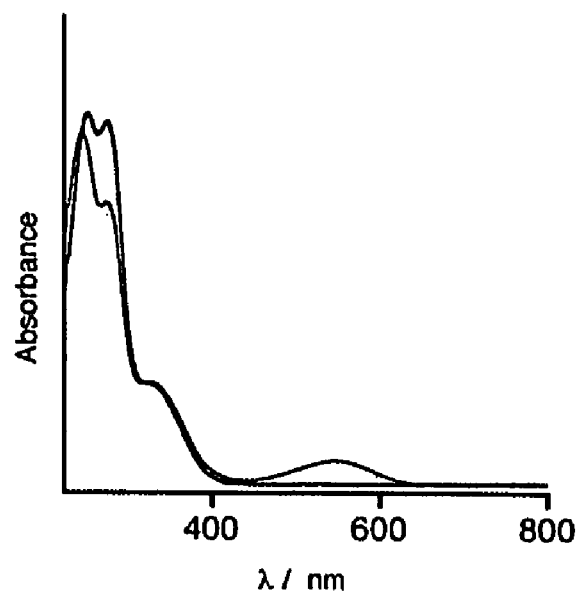
FIG. 5 is a graph of the UV-VIS absorption spectra of 1,2-bis(2,2'-bithien-3-yl)hexafluorocyclopent-1-ene (compounds 2 and 2') at the photostationary state containing 38% 2'. The spectra were of $CH_2Cl_2$ solutions at $2\times10^{-5}$ M. The photostationary state was obtained by irradiating a solution of 2 with 313 nm light until no spectral changes were observed.

The bis(dithiophene) 2 exhibits a low-energy absorption band at λ$_{max}$=320 nm (FIG. 5). The absorption band of bis (dithiophene) 2' appears at λ$_{max}$=545 nm after irradiation of a CH$_2$Cl$_2$ solution (2×10$^{-5}$ M) with 313 nm light and reaches a photostationary state of 38% in CD$_2$Cl$_2$ (1×10$^{-3}$ M) as monitored by $^1$H NMR spectroscopy (FIG. 5).

2.4 Cyclic Voltammetry of Compound 2

Figure 6:
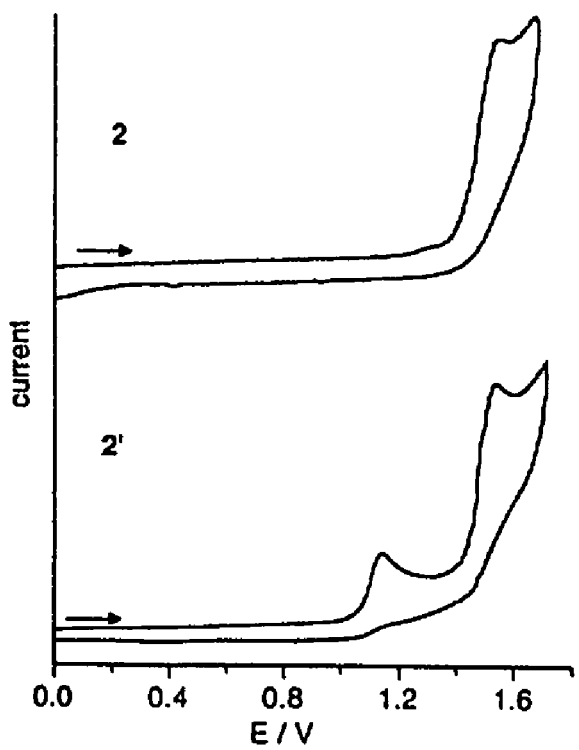
FIG. 6 are cyclic voltammograms of compounds 2 (top) and 2' (bottom) using $1\times10^{-3}$ M $CH_3CN$ solutions of both isomers at a scan rate of 200 mV/s with 0.1 M $NBu_4PF_6$ as the supporting electrolyte. A platinum disk working electrode, a Ag/AgCl (in saturated NaCl) reference electrode and a platinum wire counter electrode were used.

The voltammogram of 2 shows an irreversible oxidation peak at 1.54 V. Irradiation of the solution of 2 with 313 nm light generated 38% of the ring-open isomer (as determined by $^1$H NMR spectroscopy) and the cyclic voltammogram shows a small irreversible oxidation peak at 1.16 V due to the ring-closed isomer 2' (FIG. 6).

Example 3

3.1 Synthesis of the 1,2-bis(2,5-diphenylthien-3-yl)-hexafluorocyclopent-1-ene (compound 3)

Scheme 10

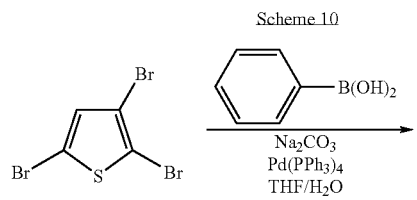

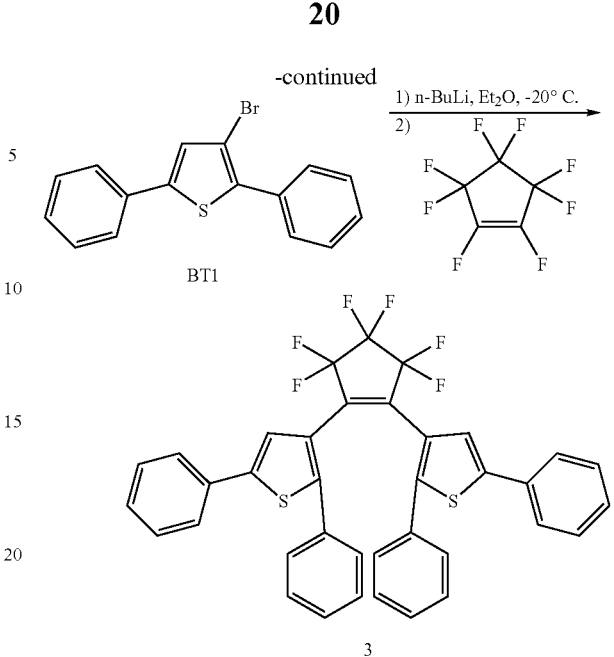

3.1.1 Synthesis of 3-bromo-2,5-diphenylthiophene (BT1)

Phenylboronic acid (0.756 g, 6.2 mmol) was added to flask containing deoxygenated THF (10 mL) and a 20% w/w Na$_2$CO$_3$ solution (10 mL) under a nitrogen atmosphere and stirred vigorously. 2,3,5-tribromothiophene (1.022 g, 3.1 mmol) and Pd(PPh$_3$)$_4$ (0.107 g, 0.096 mmol) were added and the solution was heated at reflux under a nitrogen atmosphere for 24 h. The heat source was removed, the reaction mixture was allowed to cool to room temperature and extracted with CH$_2$Cl$_2$ (3×20 mL). The combined organic extracts were washed with H$_2$O (2×20 mL) followed by brine (2×20 mL), dried (Na$_2$SO$_4$) and filtered. The solvent was evaporated under reduced pressure and the crude product was purified using column chromatography through silica gel (hexanes) yielding 0.553 g of pure product as a white solid. Yield: 57%.

M.p. 43-44° C.; $^1$H NMR (400 MHz, CD$_2$Cl$_2$) δ7.72-7.69 (m, 2H), 7.63-7.60 (m, 2H), 7.49-7.32 (m, 7H), 7.31 (s, 1H); $^{13}$C NMR (100 MHz; CDCl$_3$) δ 143.2, 137.3, 133.1, 132.8, 129.0, 128.9, 128.5, 128.3, 128.2, 127.4, 107.9 (11 of 16 carbons found); FT-IR (CH$_2$Cl$_2$ cast) 3062, 3014, 1600, 14844, 1443, 1326, 1076, 1028, 825, 759, 756, 690 cm$^{-1}$; LRMS (CI) Calcd for M$^+$ (C$_{16}$H$_{11}$BrS): 314. Found: 317 ([M+H]$^+$, [$^{81}$Br], 100%), 315 ([M+H]$^+$, [$^{79}$Br], 94%);

Anal. Calcd for C$_{16}$H$_{11}$BrS: C, 60.96; H, 3.32. Found: C, 61.11; H, 3.56.

3.1.2 Synthesis of the 1,2-bis(2,5-diphenylthien-3-yl)-hexafluorocyclopent-1-ene (compound 3)

A solution of 3-bromo-2,5-diphenylthiophene (0.200 g, 0.63 mmol) in anhydrous Et$_2$O (10 mL) cooled to –20° C. was treated with n-BuLi (0.25 mL of a 2.5 M solution in hexane) dropwise under a nitrogen atmosphere. A white precipitate formed after stirring for 5 min. This reaction mixture was stirred at –20° C. for a total of 15 min followed by addition of octafluorocyclopentene (40 μL, 0.31 mmo) using a cooled gas tight syringe. The precipitate remained therefore anhydrous THF (3 mL) was added to dissolve the precipitate. After stirring for 30 min, the cooling bath was removed and the reaction was allowed to warm to room temperature and stirred for 1 h when it was quenched with 5% HCl (5 mL). The aqueous layer was separated and extracted with Et$_2$O (2×10 mL). All organic extracts were combined, washed with H$_2$O (2×10 mL), followed by brine (10 mL), dried (Na$_2$SO$_4$) and filtered. The solvent was evaporated under reduced pressure and the crude product was purified using column chromatography through silica gel (hexanes) yielding 59 mg of pure product as a yellow crystalline solid. Yield: 30%.

M.p. 223-225° C.; $^1$H NMR (400 MHz, CD$_2$Cl$_2$) δ 7.38 (m, 8H), 7.33 (m, 2H), 7.09 (m, 6H), 7.01 (m, 6H), 6.31 (s, 2H); $^{13}$C NMR (100 MHz, CDCl$_3$) δ 144.3, 143.7, 133.3, 132.3, 128.7, 128.7, 128.0, 127.8, 127.8, 125.6, 124.4, 122.8 (12 of 15 carbons found); FT-IR (CH$_2$Cl$_2$ cast) 3069, 3014, 2924, 1600, 1490, 1448, 1324, 1269, 1186, 1124, 1097, 979, 924, 751, 690 cm$^{-1}$; LRMS (CI) Calcd for M$^+$ (C$_{37}$H$_{22}$F$_6$S$_2$): 644. Found: 645 [M+H]$^+$. Anal. Calcd for C$_{37}$H$_{22}$F$_6$S$_2$: C, 68.93; H, 3.44. Found: C, 69.20; H, 3.50.

3.1.3 Synthesis of the Ring-Closed Form 3'

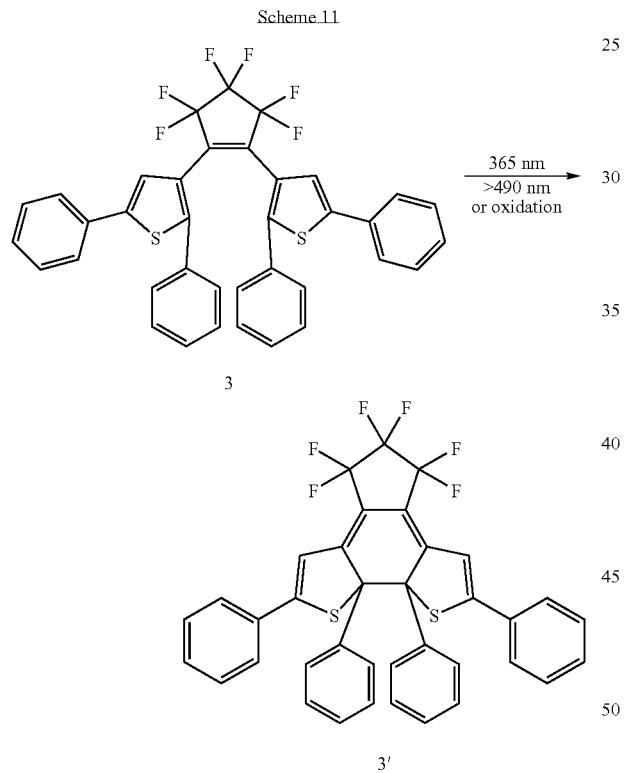

Compound 3 (0.8 mg) was dissolved in CD$_2$Cl$_2$ (1.2 mL) and placed in an NMR tube. The solution was irradiated with 365 nm light for 4 min. This resulted in a photostationary state containing 42% of the ring-closed isomer 3'.

$^1$H NMR (600 MHz, CD$_2$Cl$_2$) δ 7.80 (d, J=7.2 Hz, 4H), 7.44 (d, J=6.0 Hz, 4H), 7.40-7.38 (m, 8H), 7.23 (m, 2H), 6.69 (s, 2H).

3.2 UV-VIS Absorption Spectroscopy of Compound 3

Figure 7:
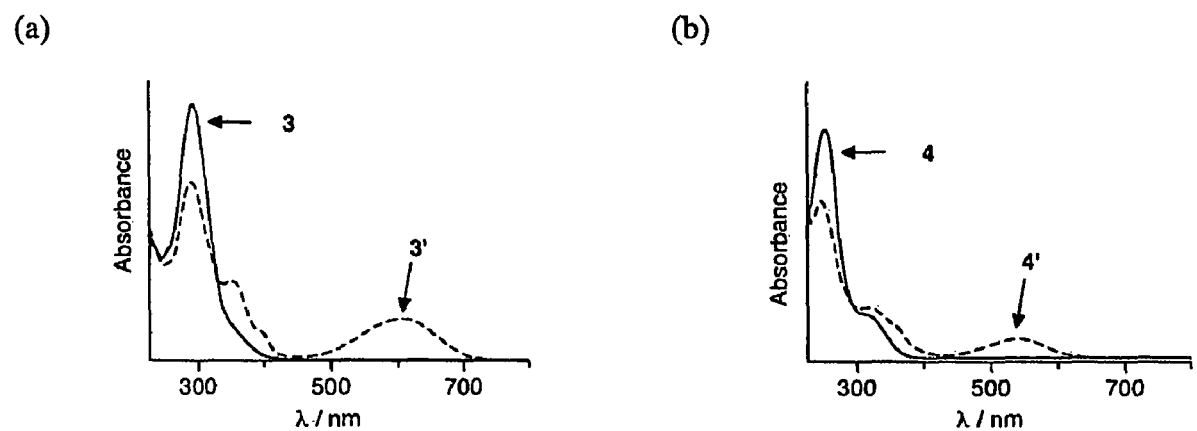
FIGS. 7(a) and (b) are graphs showing the UV-Vis absorption spectra of $CH_2Cl_2$ solutions ($2\times10^{-5}$ M) of the ring-open (—) and ring-closed ( - - - ) forms of (a) 2-bis(2,5-diphenylthien-3-yl)-hexafluorocyclopent-1-ene (compound 3) and (b) 1,2-bis(2-phenyl-3-thienyl)hexafluorocyclopent-1-ene (compound 4). The ring-closed forms were generated by irradiating with 365 nm (compound 3) and 313 nm (compound 4) light until the photostationary state was reached which consisted of 42% and 27% of the ring-closed 3' and 4', respectively.

Upon irradiation of a CH$_2$Cl$_2$ solution (2×10$^{-5}$ M) of compound 3 using 365 nm light, the colourless ring-open isomer 3 ($\lambda_{max}$=292 nm) was converted to the blue ring-closed isomer 3' ($\lambda_{max}$=604 nm) (FIG. 7a). $^1$H NMR spectroscopic analysis of the ring-closing reaction determined that the photostationary state contained 42% of the ring-closed isomer 3' when a CD$_2$Cl$_2$ solution of 3 was irradiated with 365 nm light for 2 minutes.

3.3 Cyclic Voltammetry of 3

Figure 8:
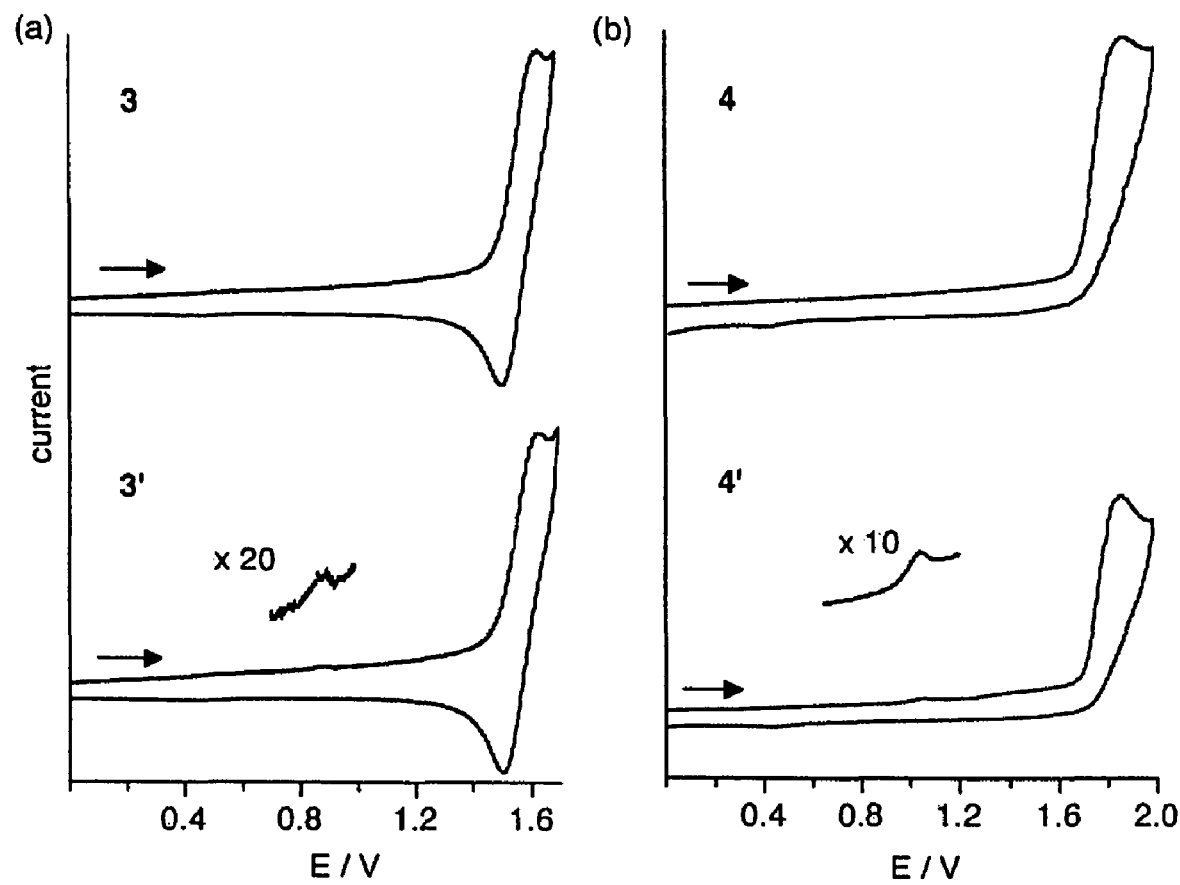
FIGS. 8(a) and (b) are cyclic voltammograms of (a) a $CH_2Cl_2$ solution ($1\times10^{-3}$ M) of 3 before irradiation (top) and after irradiation (bottom) with 365 mm light for 5 minutes and (b) a $CH_3CN$ solution ($1\times10^{-3}$ M) of compound 4 before irradiation (top) and after irradiation (bottom) with 313 nm light for 2 minutes. All voltammograms were performed at a scan rate of 200 mV/s with $NBu_4PF_6$ as the supporting electrolyte. The inset in (a) magnifies the region of the bottom voltammogram between 0.7 and 1.20 V. The inset in (b) magnifies the region of the bottom spectrum between 0.7 and 1.02 V. A platinum disk working electrode, a Ag/AgCl (in saturated NaCl) reference electrode and a platinum wire counter electrode were used.

The cyclic voltammogram of a CH$_2$Cl$_2$ solution (1×10$^{-3}$ M) of compound 3 shows an irreversible oxidation peak at 1.62 V due to the oxidation of the ring-open isomer (FIG. 8a). Irradiation of the solution with 365 nm light generated the blue ring-closed isomer and the cyclic voltammogram of this solution showed a very small irreversible oxidation peak at 0.89 V which is assigned to the ring-closed isomer 3'.

3.4 Electrochemical Ring-Opening of 3'

Electrolysis of CD$_3$CN solutions (1×10$^{-3}$ M) containing the blue ring-closed isomer 3' at 1.0 V resulted in decolourization of the solutions and $^1$H NMR analysis showed that complete conversion from the ring-closed isomer 3' to the ring-open isomer 3 resulted. Addition of only 2 mol % of the catalyst [(4-BrC$_6$H$_4$)$_3$N][SbCl$_6$] to a solution containing 3' at the photostationary state (as determined by UV-VIS spectroscopy) resulted in complete conversion to the ring-open isomer 3 indicating that the ring-opening process of this molecule is also catalytic.

Example 4

4.1 Synthesis of 1,2-bis(2-phenyl-3-thienyl) hexafluorocyclopent-1-ene (compound 4)

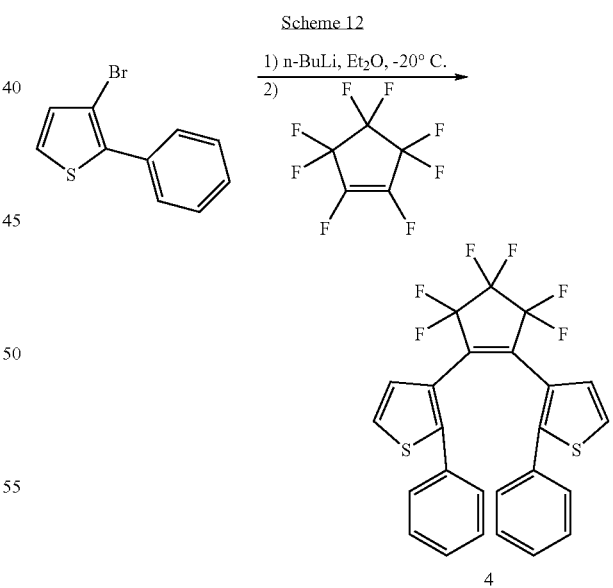

A solution of 3-bromo-2-phenylthiophene (0.4565 g, 1.9 mmol) in anhydrous Et$_2$O (25 mL) cooled to −20° C. was treated with n-BuLi (0.76 mL of a 2.5 M solution in hexane) under a nitrogen atmosphere. After stirring for 45 min, a white precipitate formed. Octafluorocyclopentene (0.119 mL, 0.95 mmol) was added via a cooled gas-tight syringe and the solution was stirred at −20° C. for 1 h. The cooling bath was removed, the reaction mixture was allowed to slowly warm to room temperature and the mixture was stirred for 16 h when it was quenched with 5% HCl (10 mL). The aqueous layer was separated and extracted with Et$_2$O (2×10 mL). All organic extracts were combined, washed with H$_2$O (2×10 mL), followed by brine (10 mL), dried (Na$_2$SO$_4$) and filtered. The solvent was evaporated under reduced pressure and the crude product was purified using column chromatography through silica gel (hexanes) yielding 83 mg of pure product as a white solid. Yield: 19%.

M.p. 117-118° C.; $^1$H NMR (500 MHz, CD$_2$Cl$_2$) δ 7.26-7.18 (m, 6H), 6.92 (m, 4H), 6.90 (d, J=5 Hz, 2H), 6.15 (d, J=5 Hz, 2H); $^{13}$C NMR (125 MHz, CD$_2$Cl$_2$) δ 145.6, 133.0, 129.0, 128.5, 128.2, 127.6, 125.6, 123.8 (8 of 13 carbons found); $^{19}$F NMR (470 MHz, CD$_2$Cl$_2$) δ-107.20 (q, J=5 Hz, 2F), −112.67 (t, J=5 Hz, 4F); FT-IR (CH$_2$Cl$_2$ cast) 3057, 1651, 1600, 1493, 1445, 1384, 1338, 1278, 1237, 1188, 1130, 1087, 1074, 1023, 1000, 965, 941, 842, 761, 746, 711, 692, 668, cm$^{-1}$; HRMS (EI) Calcd for M$^+$ (C$_{25}$H$_{14}$F$_6$S$_2$): 492.0441. Found: 492.0445.

Anal. Calcd for C$_{25}$H$_{14}$F$_6$S$_2$: C, 60.97; H, 2.87. Found: C, 60.94; H, 2.99.

4.2 Synthesis of the Ring-Closed Form 4'

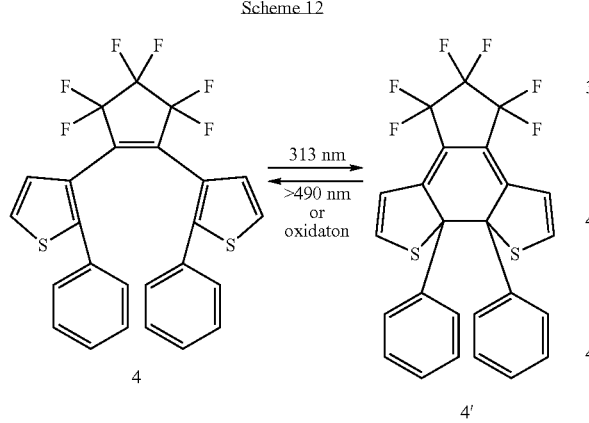

Scheme 12

Compound 4 (~5 mg) was dissolved in CH$_2$Cl$_2$ (20 mL) and placed in a quartz glass cell. The solution was irradiated with 313 nm light for 5 min. The solvent was removed under reduced pressure and the crude product was purified using column chromatography through silica gel (hexanes:CHCl$_3$, 9:1) to afford 4' as a purple solid.

$^1$H NMR (300 MHz, CD$_2$Cl$_2$) δ 7.69 (dt, J=7, 2 Hz, 4H), 7.39-7.22 (m, 5H), 7.01 (d, J=6 Hz, 2H), 6.22 (d, J=6 Hz, 2H).

4.3 UV-VIS Absorption Spectroscopy of Compound 4

Upon irradiation of a CH$_2$Cl$_2$ solution (2×10$^{-5}$ M) of 4 with 313 nm light, the colourless ring-open form 4 ($\lambda_{max}$=251 nm) was converted to the purple ring-closed isomer 4' ($\lambda_{max}$=541 nm) (FIG. 7b). $^1$H NMR spectroscopic analysis determined that the photostationary state contained 27% of the ring-closed isomer 4' when a CD$_2$Cl$_2$ solution (1×10$^{-3}$ M) of 4 was irradiated with 313 nm light for 2 minutes. The ring-opening reactions of both 3' and 4' could be done by irradiating the solutions with light using wavelengths greater than 490 nm.

4.4 Cyclic Voltammetry of Compound 4

The cyclic voltammogram of a CH$_3$CN solution (1×10$^{-3}$ M) of 4 shows an irreversible oxidation peak at 1.86 V due to the oxidation of the ring-open isomer (FIG. 8b). Irradiation of the solution with 313 nm light generated the purple ring-closed isomer and the cyclic voltammogram of this solution showed a very small irreversible oxidation peak at 1.05 V which is assigned to the ring-closed isomer 4'.

4.5 Electrochemical Ring-Opening of 4'

Electrolysis of a CD$_3$CN solution (1×10$^{-3}$ M) of 4' containing 27% of the ring-closed isomer 4' at 1.1 V for 10 minutes resulted in the decolourization of the solution and subsequent regeneration of the $^1$H NMR spectrum of the ring-open isomer 4. Addition of 8 mol % of the one-electron accepting radical cation [(4-BrC$_6$H$_4$)$_3$N][SbCl$_6$] to a CD$_2$Cl$_2$ solution (1×10$^{-5}$ M) of 4' at the photostationary state (as determined by UV-VIS spectroscopy) resulted in the complete disappearance of the absorption band in the visible region of the UV-VIS absorption spectrum and regeneration of the spectrum for the ring-open 4 indicating that the ring-opening process of this molecule is also catalytic.

Example 5

5.1 Synthesis of 1,2-bis(2-methyl-5,5'-dithiophen-3-yl)perfluorocyclopent-1-ene (compound 5)

Method 1

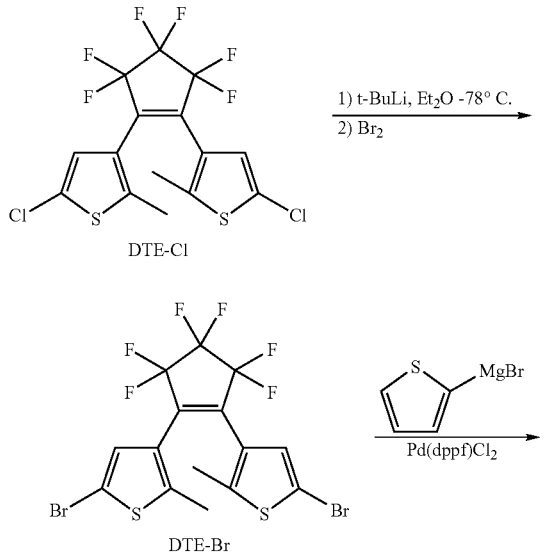

Scheme 13

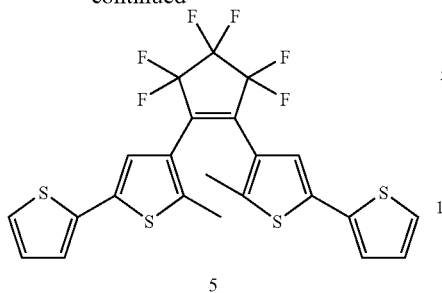

5

5.1.1 Synthesis of 1,2-bis(5-bromo-2-methylthien-3-yl)-perflourocyclopent-1-ene (DTE-Br).

A solution of dichloride DTE-CL (0.500, 1.14 mmol) in anhydrous Et$_2$O (40 mL) cooled to −78° C. was treated with t-BuLi (1.34 mL of a 1.7 M solution in pentane) dropwise under an argon atmosphere. After stirring for 30 min, a solution of Br$_2$ (0.117 mL, 2.29 mmol) in anhydrous Et$_2$O (10 mL) was added dropwise and the mixture was stirred for 20 min at −78° C. The cooling bath was removed and the reaction mixture was allowed to warm to room temperature. The reaction mixture was washed with H$_2$O (2×15 mL) followed by brine (15 mL), dried (Na$_2$SO$_4$) and filtered. The solvent was evaporated under reduced pressure and the crude product was purified using column chromatography through silica gel (hexanes) yielding 0.452 g of the pure product as a colorless crystalline solid. Yield: 75%

M.p. 146-148° C.; $^1$H NMR (300 MHz, CDCl$_3$) δ 6.99 (s, 2H), 1.87 (s, 6H); $^{13}$C NMR (100 MHz, CDCl$_3$) δ 143.3, 129.1, 125.2, 110.0, 14.4 (5 of 8 carbons found); FT-IR (CH$_2$Cl$_2$ cast) 3110, 3076, 2924, 1514, 1425, 1322, 1220, 1152, 1079, 1003, 839, 812, 785, 692 cm$^{-1}$; LRMS (EI) Calcd for M$^+$ (C$_{15}$H$_8$Br$_2$F$_6$S$_2$): 524. Found: 524 (M$^+$, [$^{79}$Br][$^{79}$Br], 52%), 526 (M$^+$, [$^{79}$Br][$^{81}$Br], 100%), 528 (M$^+$, [$^{81}$Br][$^{81}$Br], 58%). Anal. Calcd for C$_{15}$H$_8$Br$_2$F$_6$S$_2$: C, 34.23; H, 1.53. Found: C, 34.07; H, 1.56.

5.1.2 Synthesis of 1,2-bis(2-methyl-5,5'-dithiophen-3-yl)perfluorocyclopent-1-ene (compound 5)

A solution of 2-bromothiophene (0.080 g, 0.50 mmol) in anhydrous Et$_2$O (10 mL) was treated with magnesium turnings (0.014 g, 0.57 mmol) and heated at reflux for 45 min. The heat source was removed and the reaction mixture was allowed to cool to room temperature when it was added to a solution of dibromide DTE-Br (0.100 g, 0.20 mmol), Pd(dppf)Cl$_2$ (0.6 mg, 0.004 mmol) and anhydrous Et$_2$O (10 mL) cooled to 0° C. dropwise via a canula. The reaction was stirred at this temperature for 1 h, then allowed to come to room temperature and stirred for 16 h when it was quenched with 5% HCl (10 mL). The aqueous layer was separated and extracted with Et$_2$O (3×10 mL). All organic extracts were combined, washed with H$_2$O (3×10 mL), followed by brine (10 mL), dried (Na$_2$SO$_4$) and filtered. The solvent was evaporated under reduced pressure and the crude product was purified using column chromatography through silica gel (hexanes) yielding 0.056 g of pure product as a white solid.

Yield: 55%

Method 2

Scheme 14

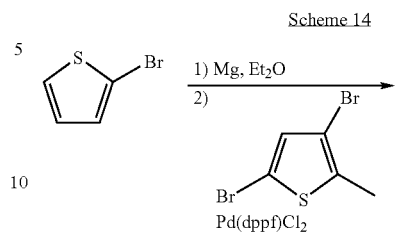

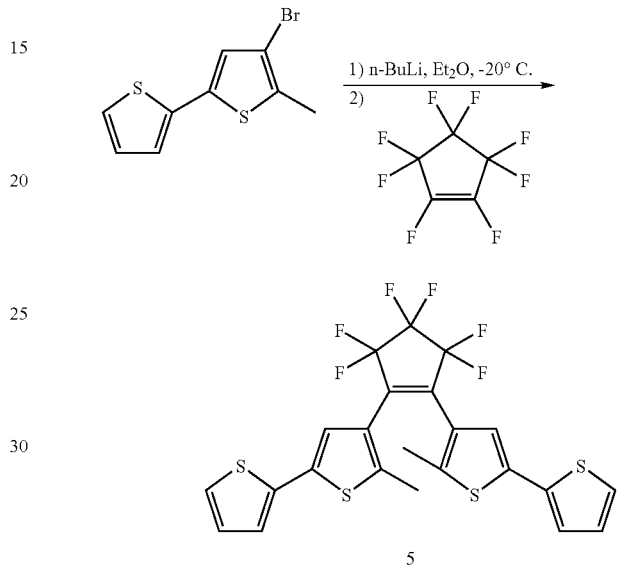

5

5.2.3 Synthesis of 4-bromo-5-methyl-[2,2']bithienyl (BT2)

A solution of 2-bromothiophene (1.44 g, 8.8 mmol) in anhydrous Et$_2$O (25 mL) was treated with magnesium turnings (0.257 g, 10.6 mmol) and heated at reflux for 45 min under a nitrogen atmosphere. The heat source was removed and the reaction mixture was allowed to cool to room temperature when it was added to a cooled (0° C.) solution of 3,5-dibromo-2-methylthiophene (2.0 g, 8.8 mmol), Pd(dppf)Cl$_2$ (13 mg, 0.018 mmol) and anhydrous Et$_2$O (10 mL) dropwise via a canula. The reaction was stirred at this temperature for 1 h, the cooling bath was removed, the mixture was allowed to slowly come to room temperature and stirred for 16 h when it was quenched with 5% HCl (10 mL). The aqueous layer was separated and extracted with Et$_2$O (2×20 mL). All organic extracts were combined, washed with H$_2$O (3×20 mL), followed by brine (20 mL), dried (Na$_2$SO$_4$) and filtered. The solvent was evaporated under reduced pressure and the crude product was purified using column chromatography through silica gel (hexanes) yielding 1.69 g of pure product as a white solid.

Yield: 78%.

M.p. 36-37° C.; $^1$H NMR (400 MHz, CD$_2$Cl$_2$) δ 7.24 (dd, J=5, 1 Hz, 1H), 7.13 (dd, J=4, 1 Hz, 1H), 7.02 (dd, J=5, 4 Hz, 1H), 7.00 (s, 1H), 2.39 (s, 3H); $^{13}$C NMR (100 MHz, CDCl$_3$) 136.4, 133.1, 127.8, 125.9, 124.6, 123.7, 109.5, 14.7 (8 of 9 carbons found); FT-IR; LRMS (CI) Calcd for M$^+$ ($C_9H_7BrS_2$): 258. Found: 261 ([M+H]$^+$, [$^{81}$Br], 92%), 259 ([M+H]$^+$, [$^{79}$Br], 100%). Anal. Calcd for $C_9H_7BrS_2$: C, 41.71; H, 2.72. Found: C, 41.96; H, 2.66.

5.2.4 Synthesis of 1,2-bis(2-methyl-5,5'-dithiophen-3-yl)perfluorocyclopent-1-ene (compound 5)

A solution of 4-bromo-5-methyl-[2,2']bithienyl BT2 (0.395 g, 1.5 mmol) in Et$_2$O (20 mL) cooled to −20° C. was treated with n-BuLi (0.61 mL of a 2.5 M solution in hexane) dropwise under a nitrogen atmosphere. After stirring for 30 min at this temperature, octafluorocyclopentene (95 μL, 0.7 mmol) was added using a cooled gas-tight syringe and the solution immediately turned dark red in color. The reaction was stirred at −20° C. for 1 h, the cooling bath was removed, the solution was slowly warmed to room temperature and stirred for an additional 16 h at this temperature. The reaction was quenched with 5% HCl (10 mL), the layers were separated and the aqueous layer was extracted with Et$_2$O (2×10 mL). The combined organic extracts were washed with H$_2$O (2×10 mL), brine (1×10 mL), dried (Na$_2$SO$_4$) and filtered. The solvent was evaporated under reduced pressure and the crude product was purified using column chromatography through silica gel (hexanes). The isolated product was recrystallized (hexanes) yielding 0.115 g of pure product as a white crystalline solid. Yield: 30%.

M.p. 126-127° C.; $^1$H NMR (600 MHz, CD$_2$Cl$_2$) δ 7.28 (dd, J=5, 1 Hz, 2H), 7.16 (dd, J=3.6, 1.2 Hz, 2H), 7.15 (s, 2H), 7.03 (dd, J=5.1, 3.6 Hz, 2H), 1.97 (s, 6H); $^{13}$C NMR (125 MHz, CDCl$_3$) δ 140.8, 136.2, 135.5, 127.9, 125.5, 124.9, 124.1, 122.8, 14.4 (9 of 12 carbons found); FT-IR (CH$_2$Cl$_2$ cast) 3117, 3076, 2952, 2910, 1440, 1426, 1338, 1275, 1192, 1138, 1115, 1053, 986, 837, 818, 742, 696 cm$^{-1}$; LRMS (CI) Calcd for M$^+$ ($C_{23}H_{14}F_6S_4$): 532. Found: 533 [M+H]$^+$; Anal. Calcd for $C_{23}H_{14}F_6S_4$: C, 51.87; H, 2.65. Found: C, 52.05; H, 2.59.

5.2.4 Synthesis of the Ring-Closed Form 5'

Compound 5 (5 mg) was dissolved in CH$_2$Cl$_2$ (50 mL) and placed in a quartz glass cell. The solution was irradiated at 365 nm for 10 min. The solvent was evaporated off under reduced pressure and the crude product purified using HPLC (hexanes) to afford the pure product 5' as a blue powder.

$^1$H NMR (300 MHz, CD$_2$Cl$_2$) δ 7.51 (dd, J=5, 1 Hz, 2H), 7.31 (dd, J=4, 1 Hz, 2H), 7.11 (dd, J=5, 4 Hz, 2H), 6.54 (s, 2H), 2.16 (s, 6H).

5.3 UV-VIS Absorption Spectroscopy of Compound 5

Figure 9:
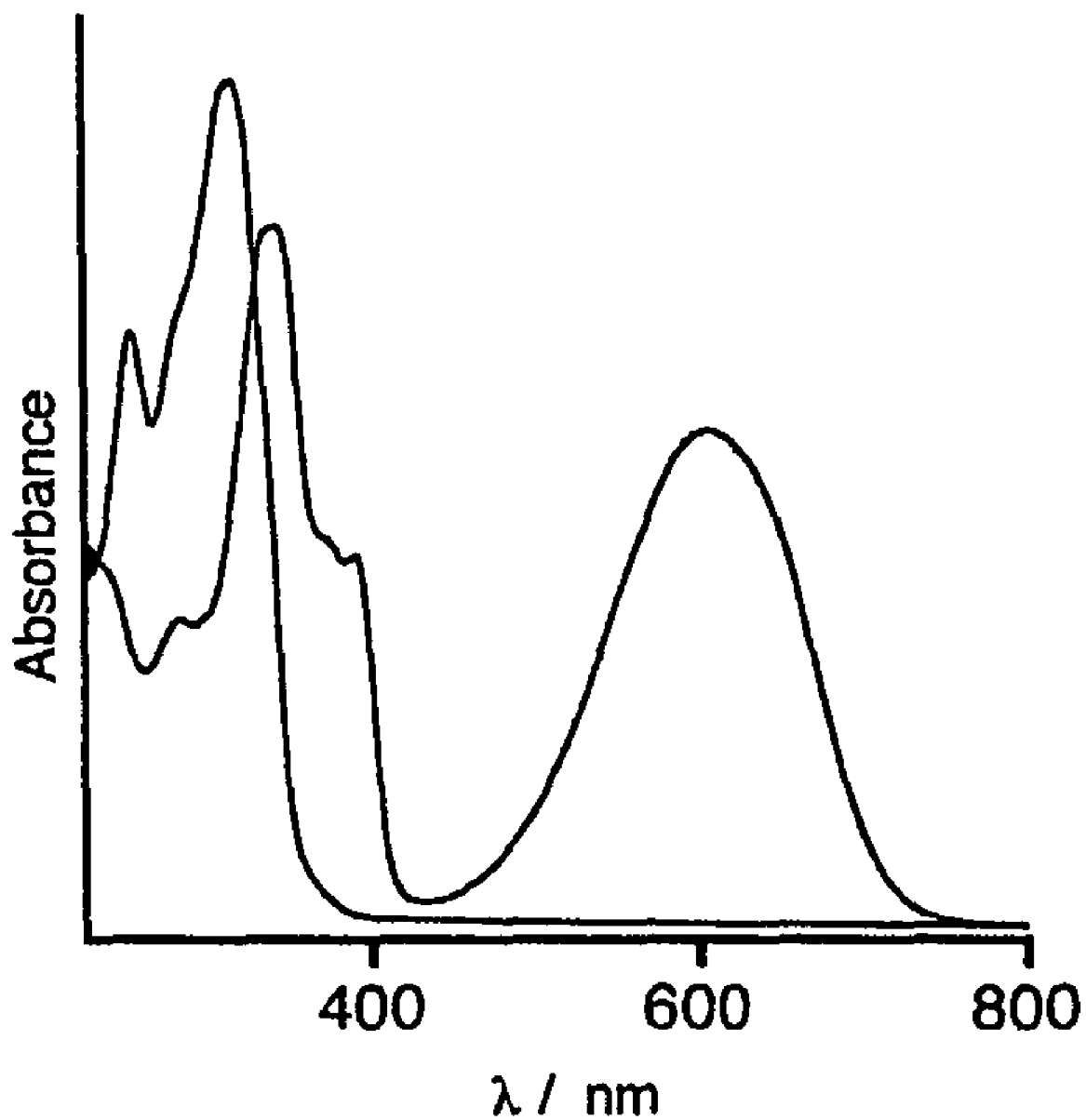
FIG. 9 is a graph of the UV-Vis absorption spectra of a $CH_2Cl_2$ solution of 1,2-bis(2-methyl-5,5'-dithiophen-3-yl) perfluorocyclopent-1-ene (compounds 5 and 5') at the photostationary state containing >97% 5'. The spectra were of $CH_2Cl_2$ solutions at $2\times10^{-5}$ M. The photostationary state was obtained by irradiating a solution of 5 with 365 nm light until no spectral changes were observed.

A solution of 5 (2×10$^{-5}$ M) in CH$_2$Cl$_2$ appears at $\lambda_{max}$=316 nm (FIG. 9). Irradiation of 5 with 365 nm light produces 5' with an absorption band at $\lambda_{max}$=625 nm. The photostationary state upon irradiation of a solution (1×10$^{-3}$M) in CD$_2$Cl$_2$ of 5 with 365 nm light is >97%. Irradiation with light greater than 490 nm resulted in the loss of colour and regeneration of the spectrum corresponding to 5.

5.4 Electrochemical Ring-Closing of Compound 5

Figure 10:
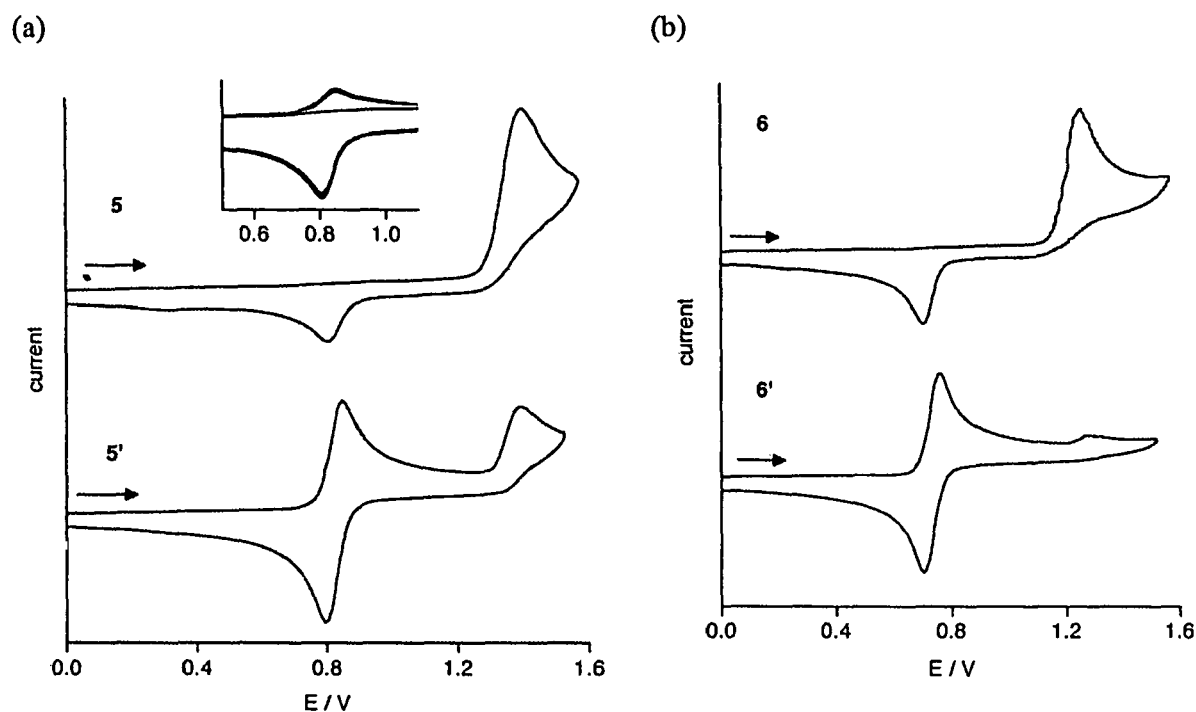
FIGS. 10(a) and 10(b) are cyclic voltammograms of a $CH_3CN$ solution ($1\times10^{-3}$ M) of (a) compound 5 (top trace), 5' (bottom trace), (b) compound 6 (top trace) and 6' (bottom trace). The inset in (a) shows the cyclic voltammogram of five redox cycles of 5. In all cases, a scan rate of 200 mV/s was used. A platinum disk working electrode, a Ag/AgCl (in saturated NaCl) reference electrode and a platinum wire counter electrode with 0.1 M $NBu_4PF_6$ as the supporting electrolyte were used.

The voltammogram of a CH$_3$CN solution (1×10$^{-3}$ M) of 5 shows an irreversible oxidation peak at 1.41 V (FIG. 10a, top trace). The voltammogram of 5' performed on a CH$_3$CN (1×10$^{-3}$ M) solution of 5 after irradiation with 365 nm light for 6 minutes shows a clear reversible anodic wave at 0.85 V due to the oxidation of the ring-closed isomer 5' (FIG. 10a, bottom trace). When the cyclic voltammetry experiment of the ring-open isomer 5 is swept through several oxidation/reduction cycles, a reversible peak appears at the same potential as that for the ring-closed isomer 5' (FIG. 10a, inset) revealing that the ring-closing reaction is induced electrochemically.

Scheme 15

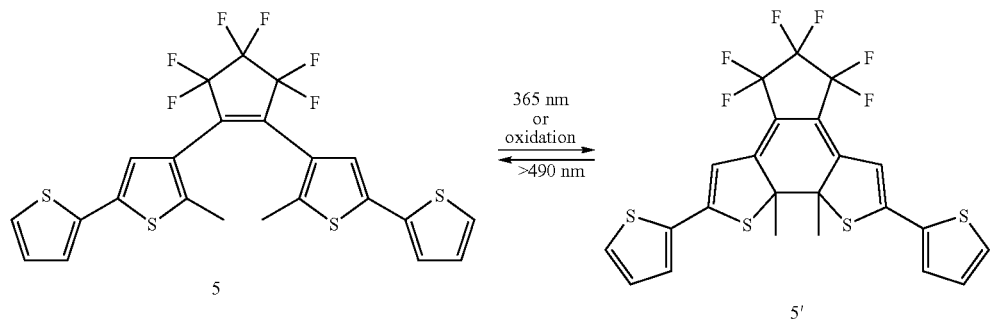

Example 6

6.1 Synthesis of 1,2-bis-(2-methyl-5,2'-dithiophen-3-yl)perfluorocyclopentene (compound 6)

Scheme 16

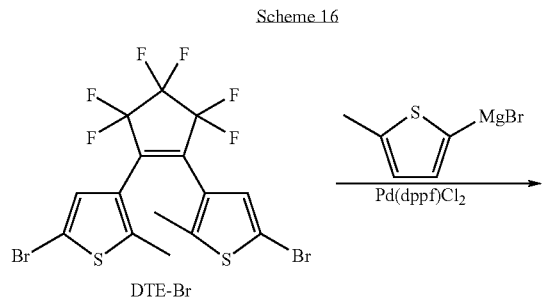

A solution of 2-bromo-5-methylthiophene (0.124 g, 0.70 mmol) in anhydrous Et$_2$O (10 mL) was treated with magnesium turnings (0.02 g, 0.83 mmol) and heated at reflux for 45 min under a nitrogen atmosphere. The heat source was removed and the reaction mixture was allowed to cool to room temperature when it was added to a cooled (0° C.) solution of dibromide DTE-Br (0.15 g, 0.29 mmol), Pd(dppf)Cl$_2$ (0.6 mg, 0.004 mmol) and anhydrous Et$_2$O (10 mL) dropwise via a canula. The reaction was stirred at this temperature for 1 h, then allowed to come to room temperature and stirred for 24 h when it was quenched with 5% HCl (10 mL). The aqueous layer was separated and extracted with Et$_2$O (3×10 mL). All organic extracts were combined, washed with H$_2$O (3×10 mL), followed by brine (10 mL), dried (Na$_2$SO$_4$) and filtered. The solvent was evaporated under reduced pressure and the crude product was purified using column chromatography through silica gel (hexanes) yielding 0.116 g of pure product as a white solid. Yield: 72%

M.p. 124-125° C.; $^1$H NMR (400 MHz, CD$_2$Cl$_2$) δ 7.05 (s, 2H), 6.94 (d, J=4 Hz, 2H), 6.69 (dq, J=3, 1 Hz, 2H), 2.47 (d, J=1 Hz, 6H), 1.94 (s, 6H); $^{13}$CNMR (125 MHz, CDCl$_3$) δ 140.2, 139.7, 135.9, 133.9, 126.0, 125.4, 123.9, 122.0, 15.3, 14.4 (10 of 13 carbons found); FT-IR (microscope) 3081, 3063, 2956, 2923, 2859, 2740, 1720.1622, 1580, 1559, 1536, 1500, 1441, 1380, 1338, 1308, 1264, 1241, 1225, 1183, 1160, 1132, 1097, 1050, 987, 901, 867, 849, 839, 827, 817, 794, 747, 738, 697, 678, 662, 623 cm$^{-1}$; HRMS (EI) Calcd for M$^+$ (C$_{25}$H$_{18}$F$_6$S$_4$): 560.0196. Found: 560.01982. Anal. Calcd for C$_{25}$H$_{18}$F$_6$S$_4$: C, 53.56; H, 3.24.

Found: C, 53.47; H, 3.26.

6.2 Synthesis of the Ring-Closed Form 6'

Scheme 17

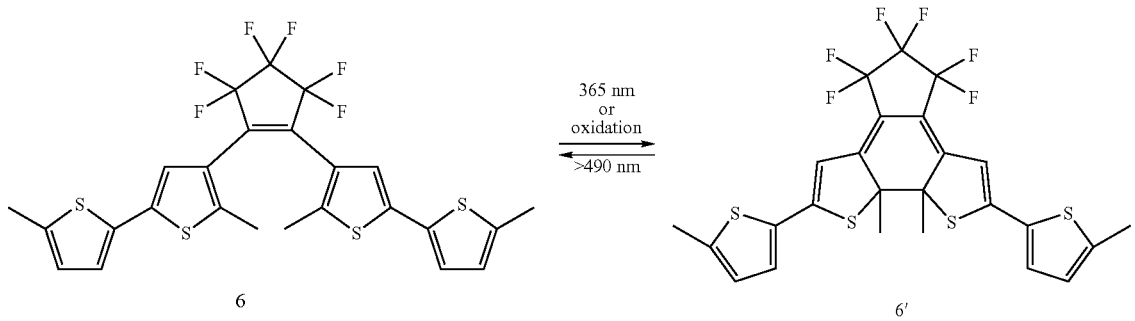

Compound 6 (1 mg) was dissolved in CD$_2$Cl$_2$ (2 mL) and placed in an NMR tube. The solution was irradiated at 365 nm for 7 min. This resulted in a photostationary state consisting of >97% of the ring-closed isomer 6'. No attempts were made to isolate 6'.

$^1$H NMR (600 MHz, CD$_2$Cl$_2$) δ 7.09 (d, J=5.4 Hz, 2H), 6.77 (dq, J=5.4, 1.2 Hz, 2H), 6.42 (s, 2H), 2.52 (s, 6H), 2.12 (s, 6H).

6.3 Cyclic Voltammetry of Compound 6

Compound 6 showed similar behaviour as compound 5 as described above. The voltammogram of 6 shows an irreversible oxidation peak at E$_{ox}$=1.26 V (FIG. 10b, top trace). Irradiation of the solution with 365 nm generated the ring-closed form 6' which shows a reversible anodic wave at E$_{1/2}$=0.74 V (FIG. 10b, bottom trace).

6.4 Electrochemical Ring-Closing of Compound 6

A colourless solution of 6 was electrolyzed at 1.35 V. Immediately after the electrolysis reaction was started, a red species was generated in the solution surrounding the platinum coil working electrode. After several seconds of electrolysis, the entire solution turned deep red in colour.

-continued

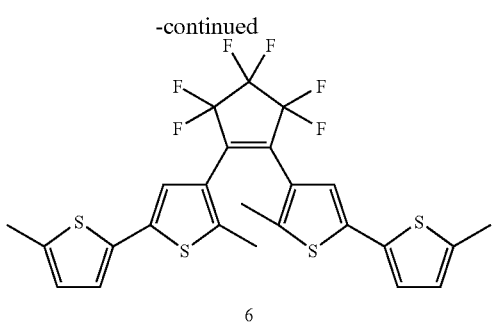

6

Although the red species produced upon electrolysis has not been characterized, we believe this to be the oxidized ring-closed form. Reduction of the solution by applying a voltage of 200-400 mV or simply opening the reaction to the atmosphere resulted in a colour change of the solution from red to blue, suggesting that the neutral ring-closed isomer was produced. The deep blue solution of 6' which was generated electrochemically can be photochemically bleached upon exposure to greater than 490 nm light for 15 minutes. Thus compound 6 is reversibly convertible between a colourless form, a red form and a blue form. This is potentially important with respect to high-density data storage media, where the three colours can represent three digital states (0, 1, 2) at the same storage location on the medium. This way more information can be stored at a single site.

Example 7

7.1 Synthesis of 2,3-bis(3-(2-methyl-5-chlorothienyl))bicyclo[2.2.1]hept-2,5-diene (compound 7)

A solution of 2-methyl-3-bromo-5-chlorothiophene in anhydrous ether (75 mL) was treated with n-butyllithium (3.6 mL, 2.5 M in hexane, 9.0 mmol) dropwise at −78° C. under an $N_2$ atmosphere. The resulting yellow solution was stirred for 30 min at this temperature then it was treated with a solution of anhydrous $ZnCl_2$ (1.23 g, 9.00 mmol) in anhydrous ether (10 mL) in one portion via a cannula (Scheme 5, above). After stirring for an additional 30 min at −78° C., the cooling bath was removed and the reaction mixture was transferred via a cannula into a frame-dried flask containing 2,3-dibromobicyclo[2.2.1]hepta-2,5-diene (750 mg, 3.00 mmol), $Pd(PPh_3)_4$ (100 mg, 0.087 mmol) and anhydrous THF (50 mL). The resulting pale yellow solution was allowed to warm slowly to room temperature and heated at reflux for 18 h under an $N_2$ atmosphere. The heating source was removed, the reaction was allowed to slowly cool to room temperature and quenched with saturated $NH_4Cl$ (50 mL). The aqueous layer was removed and extracted with ether (3×50 mL). The combined organic layers were dried ($Na_2SO_4$), filtered and concentrated to dryness in vacuo. The crude product was purified by column chromatography (hexanes) yielding 0.65 g of dichloride monomer 7 as a pale yellow solid. Yield: 62%.

M.p. 67-69° C.; $^1H$ NMR (CDCl$_3$, 400 MHz) δ 6.93 (m, 2H), 6.58 (s, 2H), 3.70 (m, 2H), 2.32 (dt, J=6, 2 Hz, 1H), 2.09 (dt, J=6, 2 Hz, 1H), 1.85 (s, 6H), $^{13}C$ NMR (CDCl$_3$, 100 MHz) δ 145.8, 142.9, 134.6, 132.6, 125.9, 71.6, 56.3, 14.1. FT-IR (KBr-cast) 2970, 2864, 1545, 1463, 1294, 1023, 970, 820, 709, 646, 468 cm$^{-1}$; MS (CI isobutane) m/z=353 [M+H]$^+$; Anal. Calcd for $C_{17}H_{14}Cl_2S_2$: C, 57.79; H, 3.99; N, 0.00. Found: C, 57.39; H, 3.84; N, 0.00.

Example 8

8.1 Synthesis of 2,3-bis(3-(2-methyl-5-carboxymethylthienyl))bicyclo[2.2.1]hept-2,5-diene (compound 8)

As shown in Scheme 5, above, a solution of dichloride monomer 7 (300 mg, 0.85 mmol) in anhydrous THF (40 mL) was treated dropwise with t-butyllithium (1.40 mL, 1.7 M in pentane, 2.40 mmol) at −78° C. until no starting material was detected by TLC. After stirring at −78° C. for 30 min, the cooling ice bath was removed and dry $CO_2$ gas was bubbled through the solution for 30 min. A white suspension immediately formed. The reaction mixture was concentrated to dryness in vacuo and re-suspended in acetone (40 mL). Solid $K_2CO_3$ (236 mg, 1.7 mmol) was added, followed by dimethylsulfate (0.2 mL, 2.13 mmol). The reaction was heated at reflux under an $N_2$ atmosphere for 18 h. The heating source was removed, the reaction was allowed to slowly cool to room temperature and quenched with water (20 mL). The acetone was removed in vacuo and the remaining aqueous solution was extracted with ether (5×30 mL). The combined organic layers were washed sequentially washed with saturated $NaHCO_3$ (10 mL) and brine (10 mL), dried ($Na_2SO_4$), filtered and evaporated to dryness in vacuo. The crude product was purified by column chromatography (9% EtOAc/hexane) yielding 150 mg of diester monomer 8 as a white solid. Yield: 44%.

M.p. 102-103.5° C. $^1H$ NMR (CDCl$_3$, 400 MHz) δ 7.49 (s, 2H), 6.97 (m, 2H), 3.84 (s, 6H), 3.75 (m, 2H), 2.37 (d, J=3 Hz, 1H,), 2.12 (d, J=3 Hz, 1H), 1.86 (s, 6H); $^{13}C$ NMR (CDCl$_3$, 100 MHz) δ 162.6, 146.2, 143.0, 142.1, 136.4, 134.5, 129.5, 71.8, 56.7, 52.0, 14.7; FTIR (KBr-cast) 2945, 2848, 1717, 1648, 1469, 1303, 1255, 1082, 745, 717 cm$^{-1}$. MS (CI isobutane) m/z=401 [M+H]$^+$, 369 [M-OCH$_3$]$^+$; Anal. Calcd for $C_{21}H_{20}O_4S_2$: C, 62.98; H, 5.03; N, 0.00. Found: C, 62.64; H, 5.31; N, 0.00.

Example 9

9.1 Synthesis of 2,3-bis(4-(5,5'-dimethyl-2,2'-bithienyl))bicyclo[2.2.1]hepta-2,5-diene (compound 9)

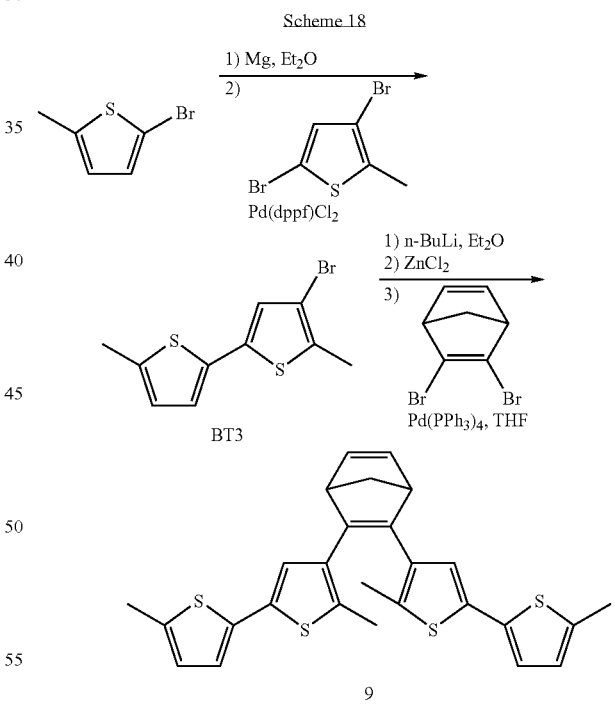

Scheme 18

9.1.1 Synthesis of 4-bromo-5,5'-dimethyl-2,2'-bithienyl (BT3)

A solution of 2-bromo-5-methylthiophene (4.00 g, 22.6 mmol) in anhydrous ether (10 mL) was treated with magnesium turnings (0.577 g, 23.7 mmol) and heated at reflux for 45 min under an $N_2$ atmosphere. The heat source was removed and the reaction mixture was slowly allowed to cool to room temperature when it was transferred to a flame-dried addition funnel via a cannula. A solution of 3,5-dibromo-2-methylthiophene (5.49 g, 21.5 mmol) and Pd(dppf)Cl$_2$ (16.5 mg, 0.023 mmol) in 75 mL anhydrous ether was treated dropwise with the solution of the Grignard reagent over 30 min at 0° C. under an N$_2$ atmosphere using an addition funnel. The resulting solution was allowed to slowly warm to room temperature and stirred for 72 h under an N$_2$ atmosphere, when it was quenched with saturated NH$_4$Cl (50 mL). The aqueous layer was separated and extracted with ether (3×75 mL). The combined organic layers were dried over Na$_2$SO$_4$, filtered and evaporated to dryness in vacuo. The crude product was purified by flash chromatography (hexanes) yielding 4.32 g of pure BT3 as a white solid. Yield: 74%.

M.p. 80-81° C.; $^1$H NMR (CDCl$_3$, 400 MHz) δ 6.89 (m, 2H), 6.64 (m, 1H), 2.47 (s, 3H), 2.37 (s, 3H); $^{13}$C NMR (CDCl$_3$, 100 MHz) δ 139.5, 134.9, 132.5, 125.9, 125.2, 123.5, 109.3, 15.3, 14.7 (9 of 10 carbons found). MS (CI isobutane) m/z=273 [M+H]$^+$.

9.1.2 Synthesis of 2,3-bis(4-(5,5'-dimethyl-2,2'-bithienyl))bicyclo[2.2.1]hepta-2,5-diene (compound 9)

A solution of 4-bromo-5,5'-dimethyl-2,2'-bithienyl BT3 (1.50 g, 5.49 mmol) in anhydrous ether was treated dropwise with n-butyllithium (2.2 mL, 2.5 M in hexane, 5.5 mmol) at −40° C. under an N$_2$ atmosphere. The resulting yellow solution was stirred for 30 min at this temperature, then it was treated with a solution of anhydrous ZnCl$_2$ (0.75 g, 5.5 mmol) in anhydrous ether (10 mL) in one portion via a cannula. After stirring for an additional 30 min at −40° C., the cooling bath was removed and the reaction mixture was transferred via a cannula into a flame-dried flask containing 2,3-dibromo[2.2.1]hepta-2,5-diene (0.500 g, 2.00 mmol), Pd(PPh$_3$)$_4$ (46 mg, 0.040 mmol) and anhydrous THF (50 mL). The resulting solution was allowed to slowly warm to room temperature and heated at reflux for 18 h under an N$_2$ atmosphere. The heat source was removed, the reaction was allowed to slowly cool to room temperature and quenched with saturated NH$_4$Cl (50 mL). The aqueous layer was removed and extracted with ether (3×75 mL). The combined organic layers were dried over Na$_2$SO$_4$, filtered and evaporated to dryness in vacuo. The crude product was purified by flash chromatography (hexanes) and crystallized from 30% hexanes in ether yielding 500 mg of monomer 9 as white platelets. Yield: 54%.

M.p. 129-130° C.; $^1$H NMR (CD$_2$Cl$_2$, 400 MHz) δ 6.98 (t, J=6 Hz, 2H), 6.83 (d, J=4 Hz, 2H), 6.61 (m, 2H), 3.77 (m, 2H), 2.43 (d, J=1 Hz, 6H), 2.36 (dt, J=6, 2 Hz, 1H), 2.09 (dt, J=6, 2 Hz, 1H), 1.89 (s, 6H); $^{13}$C NMR (CDCl$_3$, 100 MHz) δ 145.7, 143.0, 138.5, 136.0, 135.3, 133.7, 132.7, 125.7, 122.9, 122.8, 71.5, 56.4, 15.3, 14.2.

Example 10

10.1 General Polymerization Procedure

A solution of bis(tricyclohexylphosphine)benzylidene ruthenium(IV)dichloride (0.003-0.01 mmol) dissolved in dry deoxygenated THF (2 mL) was added through a cannula into a THF solution of the appropriate monomer (0.2-0.5 mmol) as shown in Scheme 5 above. The final monomer concentrations were 0.05 M. After stirring at room temperature for 18 h under a N$_2$ atmosphere, excess ethyl vinyl ether was added and the resulting solutions were stirred while exposed to the atmosphere for 30 min. The crude reaction mixtures were evaporated to dryness in vacuo. To isolate the polymers in high purity the solid residues were re-dissolved in THF (2 mL), triturated with cold methanol or ether and the precipitate collected by vacuum filtration.

10.2 Dichloride Polymer (Compound 10)

Dichloride monomer 7 (137 mg, 0.37 mmol) was polymerized with 0.02 molar equivalents of bis(tricyclohexylphosphine)benzylidene ruthenium(IV)dichloride (6.1 mg, 0.007 mmol) to afford 105 mg of polymer 10 as an off-white solid. Yield: 80%.

$^1$H NMR (CDCl$_3$, 400 MHz) δ 6.5 (br s), 5.4 (br s), 3.7 (br s), 3.5 (br s), 2.5 (br s), 1.8-1.6 (m).

Example 11

11.1 Diester Polymer (Compound 11)

Diester monomer 8 (150 mg, 0.38 mmol) was polymerized with 0.02 molar equivalents of bis(tricyclohexylphosphine) benzylidene ruthenium(IV)dichloride (6.2 mg, 0.008 mmol) to afford 92 mg of polymer 11 as an off-white solid. Yield: 60%.

$^1$H NMR (CDCl$_3$, 400 MHz) δ 5.3-5.4 (m), 3.5 (br s), 3.8 (br s), 2.5 (br s), 1.9-1.7 (m).

Example 12

12.1 Dicarboxylic Acid Polymer (Compound 12)

A solution of diester polymer 11 (31 mg) in deoxygenated THF (3 mL) was treated with deoxygenated water (1.5 mL), followed by an aqueous KOH solution (0.3 mL, 1M). The resulting solution was heated at reflux under an N$_2$ atmosphere for 5 h, the heat source was removed, the reaction was allowed to cool slowly to room temperature and stirred there for 18 h. The crude reaction mixture was concentrated to 1 mL, and acidified with 3M HCl (3 drops). The resulting precipitate was collected by vacuum filtration, washed sequentially with cold water (3 mL), Et$_2$O (3 mL) and CHCl$_3$ (3 mL) and dried in vacuo yielding 25 mg of dicarboxylate polymer 12 as an off-white solid. Yield: 83%.

$^1$H NMR (CH$_3$OD, 400 MHz) δ 7.3 (br s), 5.4 (br s), 4.2-3.4 (m), 2.5 (br s), 1.8 (br s).

Figure 11:
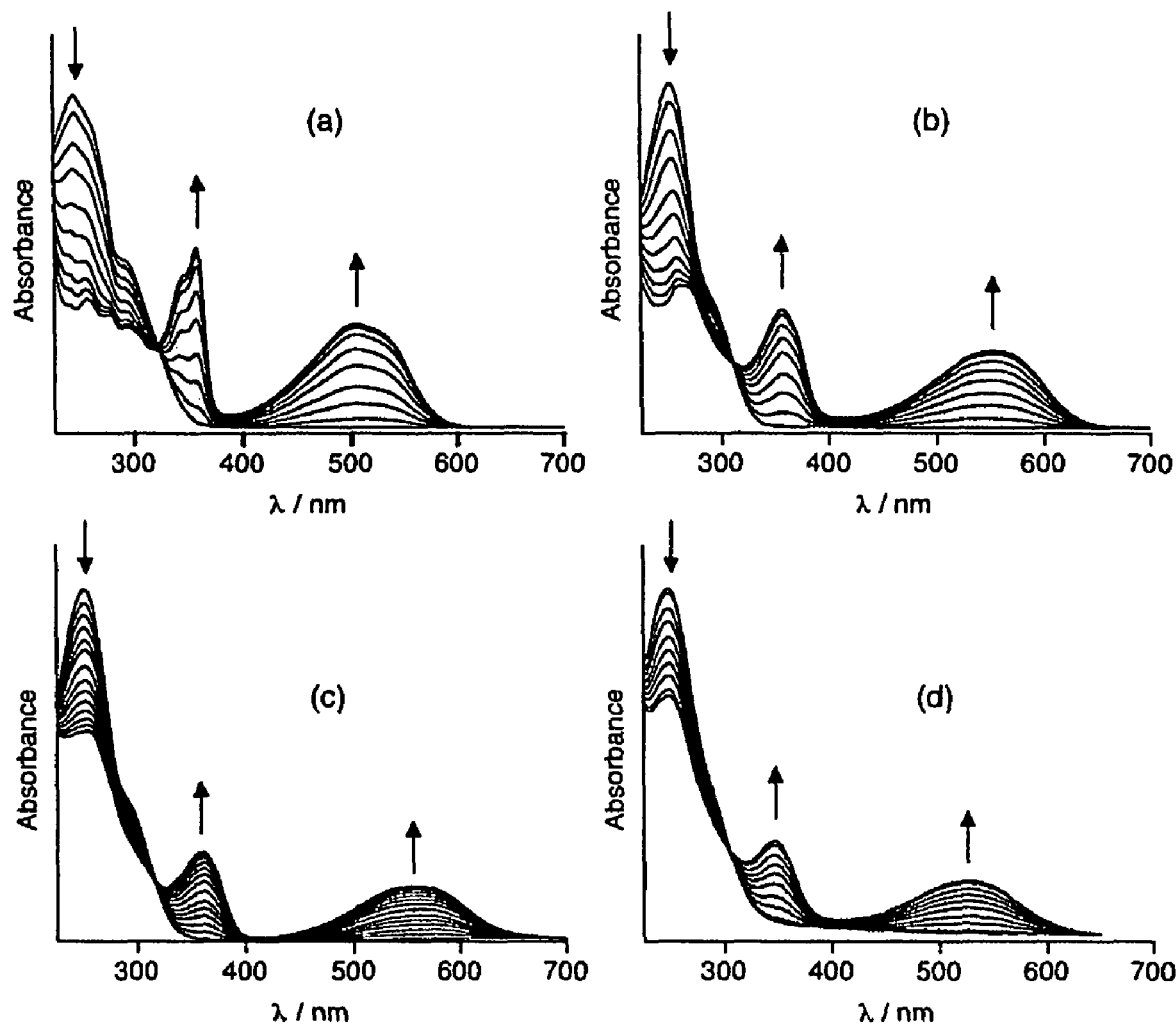
FIGS. 11(a)-(d) are UV-Vis absorption spectra showing changes in the spectra upon irradiation of (a) 2,3-bis(3-(2-methyl-5-carboxymethylthienyl))bicyclo[2.2.1]hept-2,5-diene (monomer 8) in solution (THF), (b) polymer 11 in solution (THF), (c) polymer 11 cast as a film, and (d) polymer 12 in solution (pH 7 $KH_2PO_4/K_2HPO_4$ buffer) with 313 nm light (254 nm for monomer 8). Irradiation periods for the solution studies are 0, 2, 6, 12, 20, 30, 45, 65, 90 and 120 s. Irradiation periods for the studies on the polymer film are 0, 2, 6, 12, 20, 30, 45, 65, 90, 120, 155, 195, 240, 290 s.

Representative UV spectra from typical photoisomerization studies are illustrated in FIG. 11 in respect of monomer 8 and polymers 11 and 12. All solutions were prepared at 2×10$^5$M in the active photochromic component. Polymer films were spin-coated onto 1 cm×2 cm quartz substrates as CHCl$_3$ solutions using a Laurell WS400A-6NPP/Lite spincoater.

Table 3 below shows the results of GPC analysis on selected compounds described above. With respect to the polymers reported in Table 1. The glass transition temperatures and melting temperatures of polymers 10 and 11, measured by differential scanning calorimetry (DSC), are also included. Themogravimetic analysis of polymers 10 and 11 indicated they are stable at high temperature.

The absorption spectra of THF solutions (FIG. 11 and Table 3) of polymers 10 and 11 shows that in each case the $\lambda_{max}$ values of the ring-closed form of the polymers are red-shifted when compared to the corresponding monomers 7 and 8 respectively. This effect can be attributed to the relief of ring-strain in the polymer, a direct result of the ROMP process.

The results of the photoinduced isomerization studies, carried out by irradiating the THF solutions at 254 nm or 313 nm with a hand-held UV lamp, are shown in FIG. 11. Within the first 10 seconds of irradiation, absorption bands appear between 500 and 600 nm as the photochromic monomers and polymers are converted from their colorless ring-open to their colored-closed forms.

TABLE 3

Monomer and Polymer Characterization

| compd | $M_w$ | $M_n$ | PDI ($M_w/M_n$) | $T_g$ (° C.) | $T_m$ (° C.) | $\lambda_{max}$/nm ($\epsilon \times 10^{-4}$ L mol$^{-1}$ cm$^{-1}$) | |
|---|---|---|---|---|---|---|---|
| | | | | | | ring-open form | ring-closed form[a] |
| 10 | 19200 | 15000 | 1.28 | 84 | 164 | 237 (3.03) | 455 (1.33) |
| 7 | — | — | — | — | — | 226 (2.22) | 422 (0.65) |
| 11 | 22100 | 15400 | 1.44 | 80 | 166 | 252 (3.15) | 556 (1.35) |
| 8 | — | — | — | — | — | 244 (2.97) | 504 (1.20) |
| 12[b] | — | — | — | — | — | 248 (2.31) | 527 (1.25) |

[a]Photostationary states obtained by irradiating (254 nm for 7, 8, and 10 and 313 nm for 11 and 12) THF solutions of the ring-open forms for 30 seconds.
[b]In aqueous phosphate buffer (pH 7).

After 120 seconds of irradiation at the concentration used, the increases in the visible absorption bands level off. The resulting colored solutions can be decolorized by irradiating them with broad-band light greater than 490 nm (434 nm for 7 and 10) resulting in the complete disappearance of absorption bands in the visible region. However, long irradiation times result in a small degree of photodegradation and the absorption spectra corresponding to the ring-open forms cannot be fully regenerated. This result is not surprising as we have reported how some non-fluorinated dithienylalkene derivatives are substantially less photo-fatigue resistant than their fluorinated counterparts. FIG. 11 also shows the photochromic behavior of hydrophilic polymer 12 in aqueous solution (phosphate buffer, pH 7, 25° C.). This polymer can also be reversibly colorized and decolorized.

Polymers 10 and 11 retain their photochromic behavior when spin-coated from CHCl$_3$ solutions onto quartz substrates (FIG. 11). Irradiation of the films with UV light (254 nm for 10 and 313 nm for 11) resulting in the immediate change in color indicating that the photochromic properties of the polymers were conserved in the processed state The changes in the UV-Vis absorption spectrum of each polymer were similar to those obtained in solution, with the exception that slightly longer irradiation times were required to reach the photostationary states (290 seconds compared to 120 seconds for polymer 11, for example). The percent mass of the active photochromic component in our original side-chain polymers ranges from 60-68%. The new generation main-chain polymer ranges from 93%. This is due to the ROMP reaction of the strained olefin producing the requisite cyclopentene backbone that has been shown to be so versatile.

Example 13

13.1 Dithiophene Polymer 13

Monomer 9 (99 mg, 0.21 mmol) was polymerized as shown in Scheme 5 with 0.02 molar equivalents of bis(tricyclohexylphosphine)benzylidene ruthenium(IV)dichloride (3.4 mg, 0.004 mmol) to afford 40 mg of polymer 13 as an off-white solid (40%). $^1$H NMR (CDCl$_3$, 400 MHz) δ 6.8-6.5 (m), 5.4 (br s), 3.8 (br s), 3.5 (br s), 2.5-2.3 (m), 1.8-1.6 (m).

It is expected polymer 13 will be electrochromic based on its structural similarity to compound 6 described above.

Polymer 12 is hydrophilic. Polymers 10, 11, and 13 are lipophilic.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A compound reversibly convertible between a ring-open isomer (I) and a ring-closed isomer (II):

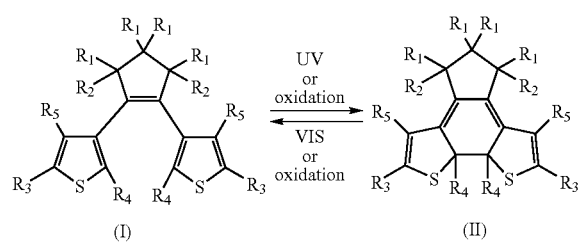

wherein:
each $R_1$ is independently selected from the group consisting of H and a halogen;
each $R_2$ is independently H, a halogen, or both
$R_2$ when taken together form CH=CH, or $R_2$ is CH=CH and forms part of a polymer backbone;
each $R_3$ is independently selected from the group consisting of H, a halogen, CO$_2$Y (Y=H, Na, alkyl, aryl),

and

(X=N,O,S);
$R_4$ is aryl; and
each $R_5$ is independently selected from the group consisting of H, alkyl and aryl, and wherein compound is convertible from said ring-open isomer (I) to said ring-closed isomer (II) under photochemical conditions and from said ring-closed isomer (II) to said ring-open isomer (I) under electrochemical conditions.

2. The compound as defined in claim 1, wherein said compound is also convertible from said ring-closed isomer (II) to ring-open isomer (I) under photochemical conditions and from said ring-open isomer (I) to said ring-closed isomer (II) under electrochemical conditions.

3. The compound as defined in claim 1, wherein said compound is also convertible from said ring-closed isomer (II) to said ring-open isomer (I) under photochemical conditions.

4. The compound as defined in claim 1, wherein said compound is also convertible from said ring-open isomer (I) to said ring-closed isomer (II) under electrochemical conditions.

5. The compound as defined in claim 1, wherein the electrochemical conversion between said isomers (II) and (I) is catalytic.

6. The compound as defined in claim 1, wherein $R_1$ is F.

7. The compound as defined in claim 1, wherein $R_1$ and $R_2$ are F, $R_3$ and $R_4$ are

(X=S) and $R_5$ is H.

8. The compound as defined in claim 1, wherein $R_1$ and $R_2$ are F, each $R_3$ is independently selected from the group consisting of aryl and

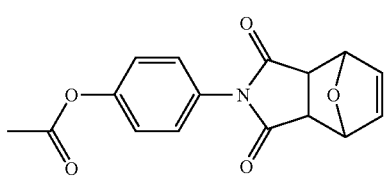

and $R_5$ is H.

9. The compound as defined in claim 1, wherein $R_1$ and $R_2$ are F, $R_3$ is H, $R_4$ is

(X=S) and $R_5$ is H.

10. The compound as defined in claim 1, wherein $R_1$ and $R_2$ are F, $R_3$ and $R_4$ are

and $R_5$ is H.

11. The compound as defined in claim 1, wherein $R_1$ is H, $R_2$ is HC=CH and forms part of the polymer backbone, $R_3$ is Cl and $R_5$ is H.

12. The compound as defined in claim 1, wherein $R_1$ is H, $R_2$ is HC=CH and forms part of the polymer backbone, $R_3$ is $CO_2CH_3$ and $R_5$ is H.

13. The compound as defined in claim 1, wherein $R_1$ is H, $R_2$ is HC=CH and forms part of the polymer backbone, $R_3$ is $CO_2H$ and $R_5$ is H.

14. A polymer comprising the compound of claim 1, wherein $R_2$ is CH=CH and forms part of the polymer backbone.

15. The polymer as defined in claim 14, wherein said polymer is a homopolymer.

16. The polymer as defined in claim 15, prepared by ring-opening methathesis polymerization.

17. A method of preparing a compound according to claim 1, comprising carrying out the reaction steps set forth in any one of:

Scheme 2:

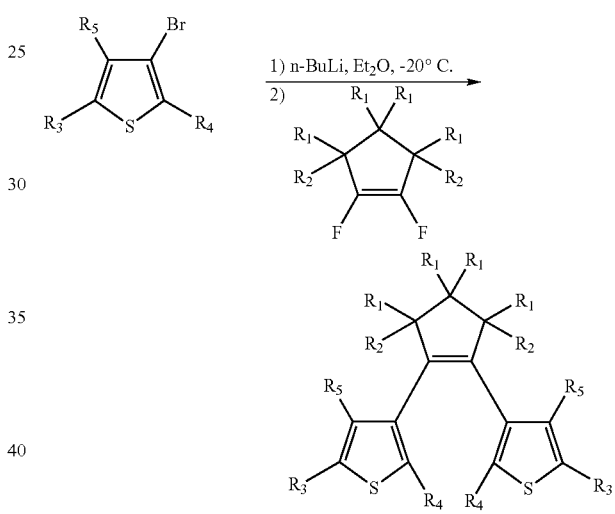

Scheme 6:

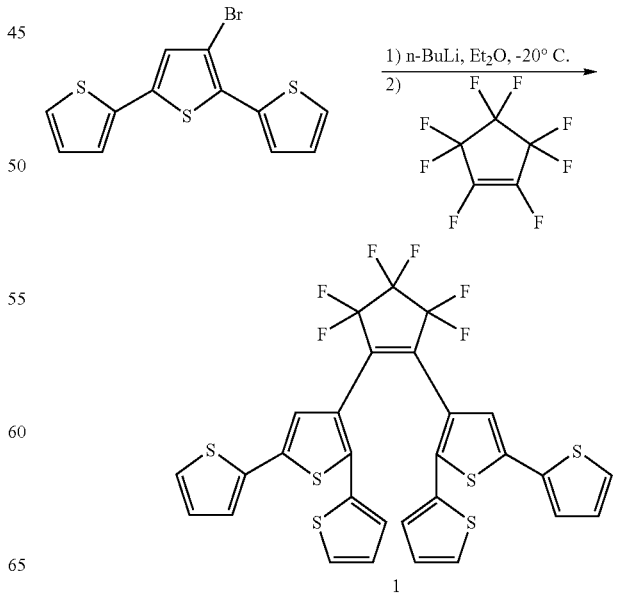

Scheme 8:

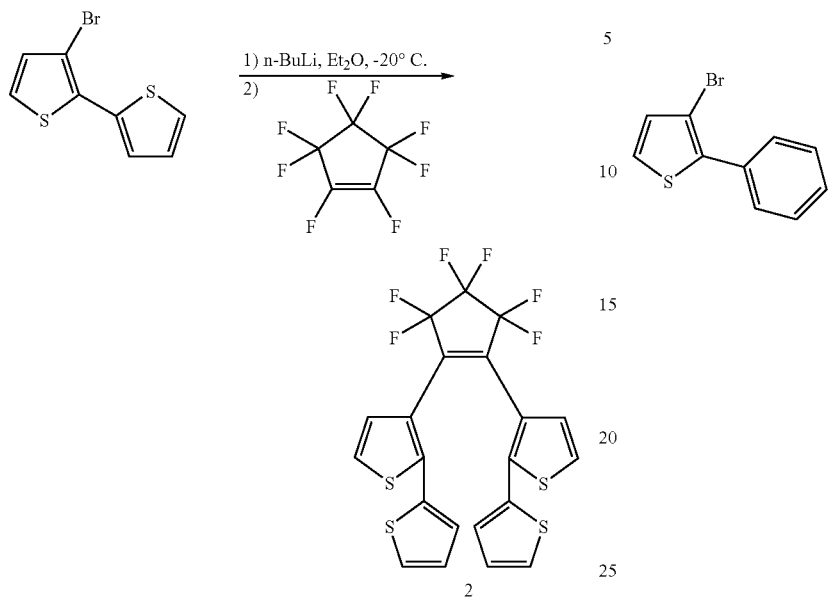

Scheme 10:

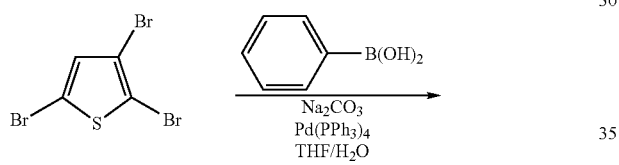

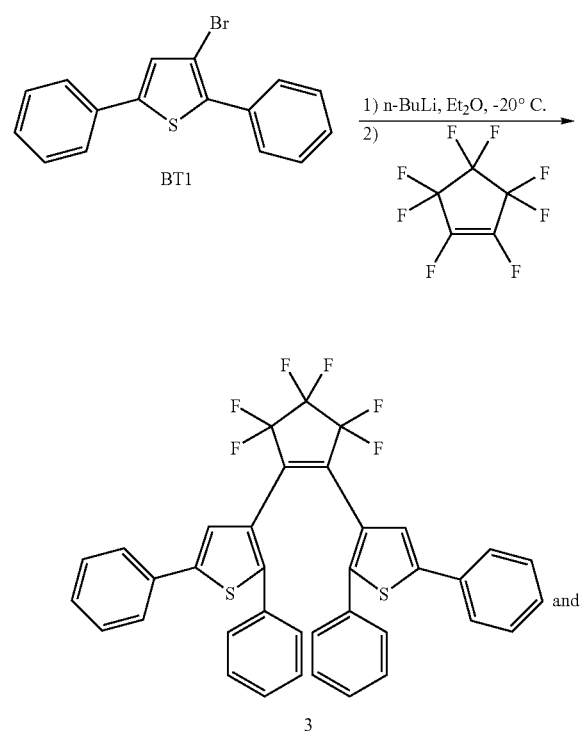

Scheme 12

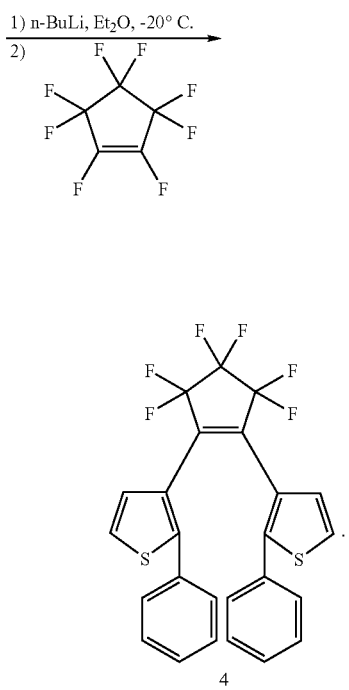

18. A method of using a compound according to claim 1 in an electrochromic and/or photochromic device.

19. The method according to claim 18, wherein said electrochromic and/or photochromic device is:
  (1) opthalmic lenses-eyeglasses that change color depending on the ambient light;
  (2) an actinometric device;
  (3) a molecular sensor;
  (4) photochromic ink;
  (5) photochromic paint;
  (6) photochromic fibers;
  (7) a variable transmission filter;
  (8) a high-density optical information storage system;
  (9) photo-regulated molecular switches that can be incorporated into molecular scale machinery;
  (10) an optoelectronic system;
  (11) a reversible holographic system; or
  (12) molecular switches in molecule-based wires and circuitry.

20. A polymer comprising a compound interconvertible between a ring-open isomer (III) and a ring-closed isomer (IV):

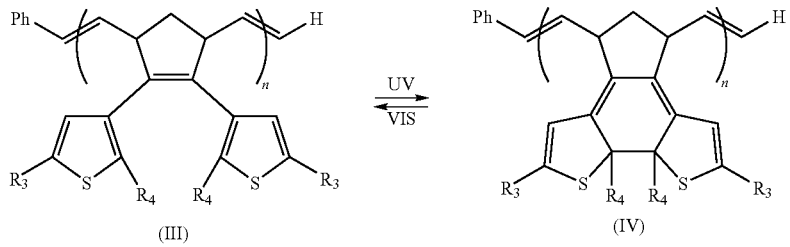

wherein each $R_3$ is independently selected from the group consisting of H, a halogen, $CO_2Y$ (Y=H, Na, alkyl, aryl),

and

(X=N,O,S) and n is between 10 and 100.

21. The polymer as defined in claim 20, wherein each $R_3$ is independently selected from the group consisting of Cl, $CO_2CH_3$ and $CO_2H$.

22. The compound as defined in claim 1, wherein:
each $R_2$ is independently H or a halogen, and
each $R_3$ is independently selected from the group consisting of H, a halogen, $CO_2Y$ (Y=aryl),

and

(X=N,O,S).

23. The compound as defined in claim 1, wherein:
each $R_2$ is independently H or F;
each $R_3$ is independently selected from the group consisting of H, a halogen

and

(X=N,O,S), and
$R_5$ is H.

24. The compound as defined in claim 1, wherein:
$R_1$ and $R_2$ are F;
each $R_3$ is independently selected from the group consisting of H and

(X=N,O,S), and
$R_5$ is H.

25. A method of preparing a polymer having electrochromic and photochromic properties, comprising utilizing a compound as defined in claim 1, wherein each $R_2$ is independently H or F, or both $R_2$ when taken together form CH=CH.

26. The polymer as defined in claim 14, wherein:
$R_1$ is F;
each $R_3$ is independently selected from the group consisting of H, a halogen, and (X=N,O,S); and
$R_5$ is H.

27. The polymer as defined in claim 14, wherein $R_1$ is F.

28. The polymer as defined in claim 14, wherein $R_1$ is F, $R_3$ and $R_4$ are

(X=S) and $R_5$ is H.

29. The polymer as defined in claim 14, wherein $R_1$ is F, $R_3$ is aryl and $R_5$ is H.

30. The polymer as defined in claim 14, wherein $R_1$ is F, $R_3$ is H, $R_4$ is

(X=S) and $R_5$ is H.

31. The polymer as defined in claim 14, wherein $R_1$ is F, $R_3$ and $R_4$ are

and $R_5$ is H.

32. A polymer comprising a main chain and the compound of claim 1, wherein each $R_2$ is independently selected from the group consisting of H and F; and each $R_3$ is independently selected from the group consisting of H, a halogen, $CO_2Y$ (Y=H, Na, alkyl, aryl),

and

(X=N,O,S), wherein at least one $R_3$ is $CO_2Y$ (Y=aryl) and links the compound to the main chain of the polymer.

33. A method of preparing a film, sheet, fiber or bead having electrochromic and photochromic properties, comprising utilizing a polymer as defined in claim 14.

34. A method of preparing a film, sheet, fiber or bead having electrochromic and photochromic properties, comprising utilizing a polymer as defined in claim 32.

35. A method of using a polymer according to claim 14 in an electrochromic and/or photochromic device.

36. A method of using a polymer according to claim 32 in an electrochromic and/or photochromic device.

* * * * *